United States Patent
Joshi et al.

(10) Patent No.: US 8,735,302 B2
(45) Date of Patent: May 27, 2014

(54) HIGH PRODUCTIVITY COMBINATORIAL OXIDE TERRACING AND PVD/ALD METAL DEPOSITION COMBINED WITH LITHOGRAPHY FOR GATE WORK FUNCTION EXTRACTION

(75) Inventors: Amol Joshi, Sunnyvale, CA (US); John Foster, Mountain View, CA (US); Zhendong Hong, San Jose, CA (US); Olov Karlsson, San Jose, CA (US); Bei Li, Fremont, CA (US); Usha Raghuram, Saratoga, CA (US)

(73) Assignee: Intermolecular, Inc., San Jose, CA (US)

( * ) Notice: Subject to any disclaimer, the term of this patent is extended or adjusted under 35 U.S.C. 154(b) by 97 days.

(21) Appl. No.: 13/480,023

(22) Filed: May 24, 2012

(65) Prior Publication Data

US 2013/0316472 A1 Nov. 28, 2013

(51) Int. Cl.
*H01L 21/31* (2006.01)
*H01L 21/469* (2006.01)

(52) U.S. Cl.
USPC ........... 438/769; 438/678; 438/680; 438/712; 438/745; 257/E21.006; 257/E21.027; 257/E21.127; 257/E21.129; 257/E21.17; 257/E21.218; 257/E21.267; 257/E21.278; 257/E21.311

(58) Field of Classification Search
USPC ......... 438/769, 678, 680, 712, 745, 724, 744, 438/756, 752, 753, 197, 238, 474, 475, 513, 438/905; 257/E21.006, E21.027, E21.127, 257/E21.129, E21.17, E21.218, E21.267, 257/E21.278, E21.311
See application file for complete search history.

(56) References Cited

U.S. PATENT DOCUMENTS

| | | | | |
|---|---|---|---|---|
| 7,947,531 B1* | 5/2011 | Chiang | ......................... | 438/116 |
| 8,449,681 B2* | 5/2013 | Duong et al. | ................. | 134/1.3 |
| 8,486,821 B1* | 7/2013 | Endo et al. | .................... | 438/597 |
| 8,524,581 B2* | 9/2013 | Kraus et al. | ................... | 438/503 |
| 8,528,608 B2* | 9/2013 | Kelekar et al. | ................. | 141/95 |
| 8,554,507 B2* | 10/2013 | Phatak | ......................... | 702/123 |

OTHER PUBLICATIONS

Wen, H., et al.; Comparison of Effective Work Function Extraction Methods Using Capacitance and Current Measurement Techniques; Jul. 1, 2006; SEMATECH; IEEE Electron Device Letters vol. 27 No. 7 pp. 298601.
Yen, F., et al.; Effective Work Function Engineering of TaxCy Metal Gate on Hfbased Dielectrics; Mar. 1, 2007; TSMC; IEEE Electron Device Letters vol. 28 No. 3 pp. 201203.
Kaushik, V., et al.; Estimation of Fixed Charge Densities in HafniumSilicate Gate Dielectrics; Oct. 1, 2006; Freescale Semiconductor, Inc.; IEEE Transactions on Electron Devices vol. 53 No. 10 pp. 26272633.

* cited by examiner

Primary Examiner — David Nhu

(57) ABSTRACT

Metal gate high-k capacitor structures with lithography patterning are used to extract gate work function using a combinatorial workflow. Oxide terracing, together with high productivity combinatorial process flow for metal deposition can provide optimum high-k gate dielectric and metal gate solutions for high performance logic transistors. The high productivity combinatorial technique can provide an evaluation of effective work function for given high-k dielectric metal gate stacks for PMOS and NMOS transistors, which is critical in identifying and selecting the right materials.

20 Claims, 17 Drawing Sheets

HIGH PRODUCTIVITY COMBINATORIAL OXIDE TERRACING AND PVD/ALD METAL DEPOSITION COMBINED WITH LITHOGRAPHY FOR GATE WORK FUNCTION EXTRACTION

TECHNICAL FIELD

The present invention relates generally to combinatorial methods for device process development. More specifically, combinatorial methods of developing fabrication processes for gate stacks including high-k gate dielectric and metal gate electrode devices with regard to device performance, such as effective work function of the gate stacks.

BACKGROUND OF THE INVENTION

Advances in semiconductor processing have demanded ever-increasing high functional density with continuous size scaling. This scaling process has led to the adoption of high-k gate dielectrics and metal gate electrodes in metal gate stacks in semiconductor devices.

High-k gate dielectrics can offer a way to scale down the thickness of the gate dielectric with acceptable gate leakage current. The use of high-k gate dielectrics is often accompanied by a metal gate electrode, since thin gate dielectric layers may cause poly depletion, affecting the device operation and performance. Metal gate electrodes further have an advantage of higher electrical conductance, as compared to poly gates, and thus can improve signal propagation times.

The manufacture of high-k dielectric devices entails the integration and sequencing of many unit processing steps, with potential new process developments, since in general, high-k gate dielectrics are much more sensitive to process conditions than silicon dioxide. For example, different combinations of high-k dielectric and metal electrode can exhibit different device characteristics such as effective work function, affecting subsequent fabrication processes, and consequently the performance of the high-k gate structures. The precise sequencing and integration of the unit processing steps enables the formation of functional devices meeting desired performance metrics such as power efficiency, signal propagation, and reliability.

As part of the discovery, optimization and qualification of each unit process, it is desirable to be able to i) test different materials, ii) test different processing conditions within each unit process module, iii) test different sequencing and integration of processing modules within an integrated processing tool, iv) test different sequencing of processing tools in executing different process sequence integration flows, and combinations thereof in the manufacture of devices such as integrated circuits. In particular, there is a need to be able to test i) more than one material, ii) more than one processing condition, iii) more than one sequence of processing conditions, iv) more than one process sequence integration flow, and combinations thereof, collectively known as "combinatorial process sequence integration", on a single monolithic substrate without the need of consuming the equivalent number of monolithic substrates per material(s), processing condition(s), sequence(s) of processing conditions, sequence(s) of processes, and combinations thereof. This can greatly improve both the speed and reduce the costs associated with the discovery, implementation, optimization, and qualification of material(s), process(es), and process integration sequence(s) required for manufacturing.

Systems and methods for High Productivity Combinatorial (HPC) processing are described in U.S. Pat. No. 7,544,574 filed on Feb. 10, 2006, U.S. Pat. No. 7,824,935 filed on Jul. 2, 2008, U.S. Pat. No. 7,871,928 filed on May 4, 2009, U.S. Pat. No. 7,902,063 filed on Feb. 10, 2006, and U.S. Pat. No. 7,947,531 filed on Aug. 28, 2009 which are all herein incorporated by reference. Systems and methods for HPC processing are further described in U.S. patent application Ser. No. 11/352,077 filed on Feb. 10, 2006, claiming priority from Oct. 15, 2005, U.S. patent application Ser. No. 11/419,174 filed on May 18, 2006, claiming priority from Oct. 15, 2005, U.S. patent application Ser. No. 11/674,132 filed on Feb. 12, 2007, claiming priority from Oct. 15, 2005, and U.S. patent application Ser. No. 11/674,137 filed on Feb. 12, 2007, claiming priority from Oct. 15, 2005 which are all herein incorporated by reference.

HPC processing techniques have been successfully adapted to wet chemical processing such as etching and cleaning. HPC processing techniques have also been successfully adapted to deposition processes such as physical vapor deposition (PVD), atomic layer deposition (ALD), and chemical vapor deposition (CVD). However, HPC processing techniques have not been successfully adapted to the development of gate stack characteristics, such as effective work function, to evaluate materials and process conditions for optimal high-k device performance.

Therefore, there is a need to apply high productivity combinatorial techniques to the development and investigation of electrical data such as effective work function for the manufacture of high-k devices.

SUMMARY OF THE DESCRIPTION

In some embodiments, the present invention discloses high productivity combinatorial (HPC) methods and systems for extracting gate work function. The methods comprise a combinatorial oxide terracing, and a combinatorial metal deposition, together with lithography patterning for forming capacitor device structures.

In some embodiments, the present invention discloses lithography patterned terracing structures, comprising varying the oxide terrace and/or the gate electrode in a combinatorial manner. Active areas can be prepared on a substrate using a lithography patterning step. An oxide layer can be formed in the active areas, and then etched to form terraced oxide in multiple site isolated regions. High-k gate dielectric layers followed by a metal electrode are then formed on the terrace oxide. The metal electrode is patterned using lithography to form gate electrodes in the multiple site isolated regions. Each site isolated region can comprise a variation of gate electrodes corresponded to a variation of the oxide terrace. High throughput screening of gate work function values can be accomplished.

BRIEF DESCRIPTION OF THE DRAWINGS

To facilitate understanding, identical reference numerals have been used, where possible, to designate identical elements that are common to the figures. The drawings are not to scale and the relative dimensions of various elements in the drawings are depicted schematically and not necessarily to scale.

The techniques of the present invention can readily be understood by considering the following detailed description in conjunction with the accompanying drawings, in which.

DETAILED DESCRIPTION

A detailed description of one or more embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to the embodiments has not been described in detail to avoid unnecessarily obscuring the description.

In some embodiments, the present invention discloses a combinatorial method to extract gate work function values from metal gate stacks including a metal electrode layer disposed on a high-k gate dielectric layer. The metal gate stacks are fabricated as patterned MOSCAP (metal oxide semiconductor capacitor) structures with oxide terracing for improved accuracy in effective work function value extraction, and with field oxide isolation for edge defect protection.

In the following description, illustrative methods for determining effective work function values are illustrated using simple planar structures and process flows. Those skilled in the art will appreciate that the description and teachings to follow can be readily applied to any simple or complex testing methodology. The drawings are for illustrative purposes only and do not limit the application of the present invention.

"Combinatorial Processing" generally refers to techniques of differentially processing multiple regions of one or more substrates. Combinatorial processing generally varies materials, unit processes or process sequences across multiple regions on a substrate. The varied materials, unit processes, or process sequences can be evaluated (e.g., characterized) to determine whether further evaluation of certain process sequences is warranted or whether a particular solution is suitable for production or high volume manufacturing.

Figure 1:
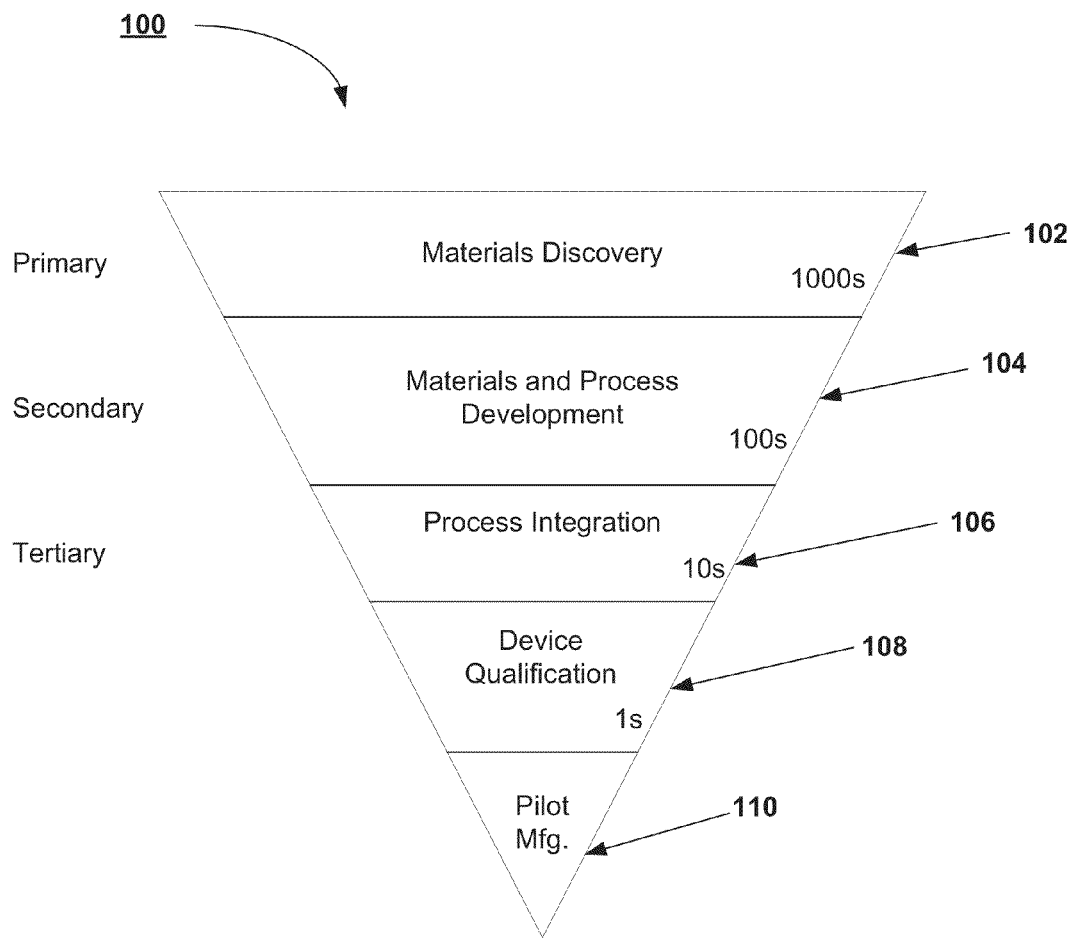
FIG. 1 illustrates a schematic diagram for implementing combinatorial processing and evaluation using primary, secondary, and tertiary screening.

FIG. 1 illustrates a schematic diagram for implementing combinatorial processing and evaluation using primary, secondary, and tertiary screening. The schematic diagram, 100, illustrates that the relative number of combinatorial processes run with a group of substrates decreases as certain materials and/or processes are selected. Generally, combinatorial processing includes performing a large number of processes during a primary screen, selecting promising candidates from those processes, performing the selected processing during a secondary screen, selecting promising candidates from the secondary screen for a tertiary screen, and so on. In addition, feedback from later stages to earlier stages can be used to refine the success criteria and provide better screening results.

For example, thousands of materials are evaluated during a materials discovery stage, 102. Materials discovery stage, 102, is also known as a primary screening stage performed using primary screening techniques. Primary screening techniques may include dividing substrates into coupons and depositing materials using varied processes. The materials are then evaluated, and promising candidates are advanced to the secondary screen, or materials and process development stage, 104. Evaluation of the materials is performed using metrology tools such as electronic testers and imaging tools (i.e., microscopes).

The materials and process development stage, 104, may evaluate hundreds of materials (i.e., a magnitude smaller than the primary stage) and may focus on the processes used to deposit or develop those materials. Promising materials and processes are again selected, and advanced to the tertiary screen or process integration stage, 106, where tens of materials and/or processes and combinations are evaluated. The tertiary screen or process integration stage, 106, may focus on integrating the selected processes and materials with other processes and materials.

The most promising materials and processes from the tertiary screen are advanced to device qualification, 108. In device qualification, the materials and processes selected are evaluated for high volume manufacturing, which normally is conducted on full substrates within production tools, but need not be conducted in such a manner. The results are evaluated to determine the efficacy of the selected materials and processes. If successful, the use of the screened materials and processes can proceed to pilot manufacturing, 110.

The schematic diagram, 100, is an example of various techniques that may be used to evaluate and select materials and processes for the development of new materials and processes. The descriptions of primary, secondary, etc. screening and the various stages, 102-110, are arbitrary and the stages may overlap, occur out of sequence, be described and be performed in many other ways.

This application benefits from High Productivity Combinatorial (HPC) techniques described in U.S. patent application Ser. No. 11/674,137 filed on Feb. 12, 2007 which is hereby incorporated for reference in its entirety. Portions of the '137 application have been reproduced below to enhance the understanding of the present invention. The embodiments described herein enable the application of combinatorial techniques to process sequence integration in order to arrive at a globally optimal sequence of high-k device fabrication process with metal gate by considering interaction effects between the unit manufacturing operations, the process conditions used to effect such unit manufacturing operations, hardware details used during the processing, as well as materials characteristics of components utilized within the unit manufacturing operations. Rather than only considering a series of local optimums, i.e., where the best conditions and materials for each manufacturing unit operation is considered in isolation, the embodiments described below consider interactions effects introduced due to the multitude of processing operations that are performed and the order in which such multitude of processing operations are performed when fabricating a high-k device. A global optimum sequence order is therefore derived, and as part of this derivation, the unit processes, unit process parameters and materials used in the unit process operations of the optimum sequence order are also considered.

The embodiments described further analyze a portion or sub-set of the overall process sequence used to manufacture a semiconductor device. Once the subset of the process sequence is identified for analysis, combinatorial process sequence integration testing is performed to optimize the materials, unit processes, hardware details, and process sequence used to build that portion of the device or structure. During the processing of some embodiments described herein, structures are formed on the processed substrate which are equivalent to the structures formed during actual production of the high-k device. For example, such structures may include, but would not be limited to, high-k dielectric layers, metal gate layers, spacers, or any other series of layers or unit processes that create an intermediate structure found on semiconductor devices. While the combinatorial processing varies certain materials, unit processes, hardware details, or process sequences, the composition or thickness of the layers or structures or the action of the unit process, such as cleaning, surface preparation, deposition, surface treatment, etc. is substantially uniform through each discrete region. Furthermore, while different materials or unit processes may be used for corresponding layers or steps in the formation of a structure in different regions of the substrate during the combinatorial processing, the application of each layer or use of a given unit process is substantially consistent or uniform throughout the different regions in which it is intentionally applied. Thus, the processing is uniform within a region (inter-region uniformity) and between regions (intra-region uniformity), as desired. It should be noted that the process can be varied between regions, for example, where a thickness of a layer is varied or a material may be varied between the regions, etc., as desired by the design of the experiment.

The result is a series of regions on the substrate that contain structures or unit process sequences that have been uniformly applied within that region and, as applicable, across different regions. This process uniformity allows comparison of the properties within and across the different regions such that the variations in test results are due to the varied parameter (e.g., materials, unit processes, unit process parameters, hardware details, or process sequences) and not the lack of process uniformity. In the embodiments described herein, the positions of the discrete regions on the substrate can be defined as needed, but are preferably systematized for ease of tooling and design of experimentation. In addition, the number, variants and location of structures within each region are designed to enable valid statistical analysis of the test results within each region and across regions to be performed.

Figure 2:
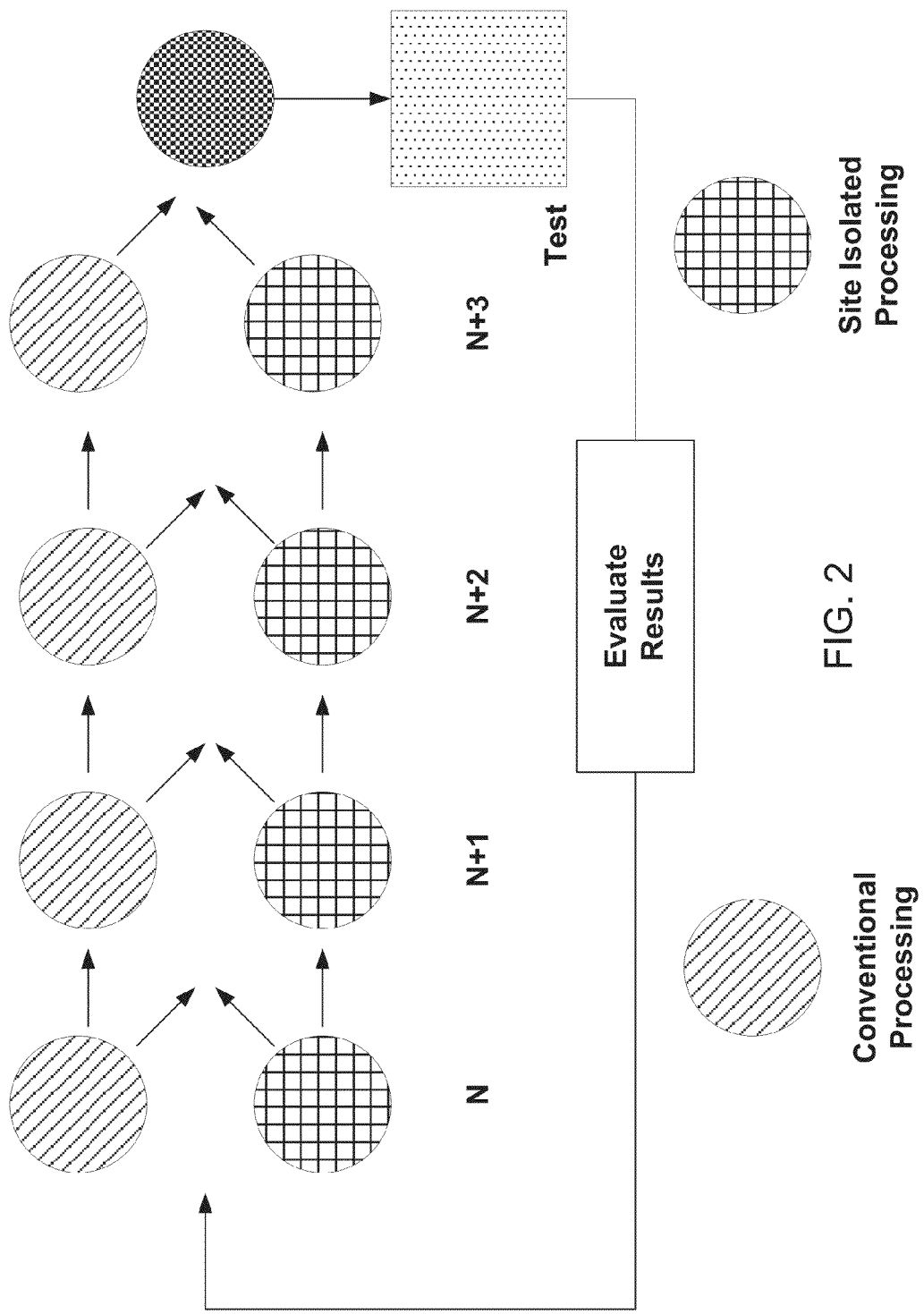
FIG. 2 is a simplified schematic diagram illustrating a general methodology for combinatorial process sequence integration that includes site isolated processing and/or conventional processing in accordance with one embodiment of the invention.

FIG. 2 is a simplified schematic diagram illustrating a general methodology for combinatorial process sequence integration that includes site isolated processing and/or conventional processing according to some embodiments. In some embodiments, the substrate is initially processed using conventional process N. In some embodiments, the substrate is then processed using site isolated process N+1. During site isolated processing, an HPC module may be used, such as the HPC module described in U.S. patent application Ser. No. 11/352,077 filed on Feb. 10, 2006. The substrate can then be processed using site isolated process N+2, and thereafter processed using conventional process N+3. Testing is performed and the results are evaluated. The testing can include physical, chemical, acoustic, magnetic, electrical, optical, etc. tests. From this evaluation, a particular process from the various site isolated processes (e.g. from steps N+1 and N+2) may be selected and fixed so that additional combinatorial process sequence integration may be performed using site isolated processing for either process N or N+3. For example, a next process sequence can include processing the substrate using site isolated process N, conventional processing for processes N+1, N+2, and N+3, with testing performed thereafter.

It should be appreciated that various other combinations of conventional and combinatorial processes can be included in the processing sequence with regard to FIG. 2. That is, the combinatorial process sequence integration can be applied to any desired segments and/or portions of an overall process flow. Characterization, including physical, chemical, acoustic, magnetic, electrical, optical, etc. testing, can be performed after each process operation, and/or series of process operations within the process flow as desired. The feedback provided by the testing is used to select certain materials, processes, process conditions, and process sequences and eliminate others. Furthermore, the above flows can be applied to entire monolithic substrates, or portions of monolithic substrates such as coupons.

Under combinatorial processing operations the processing conditions at different regions can be controlled independently. Consequently, process material amounts, reactant species, processing temperatures, processing times, processing pressures, processing flow rates, processing powers, processing reagent compositions, the rates at which the reactions are quenched, deposition order of process materials, process sequence steps, hardware details, etc., can be varied from region to region on the substrate. Thus, for example, when exploring materials, a processing material delivered to a first and second region can be the same or different. If the processing material delivered to the first region is the same as the processing material delivered to the second region, this processing material can be offered to the first and second regions on the substrate at different concentrations. In addition, the material can be deposited under different processing parameters. Parameters which can be varied include, but are not limited to, process material amounts, reactant species, processing temperatures, processing times, processing pressures, processing flow rates, processing powers, processing reagent compositions, the rates at which the reactions are quenched, atmospheres in which the processes are conducted, an order in which materials are deposited, hardware details of the gas distribution assembly, etc. It should be appreciated that these process parameters are exemplary and not meant to be an exhaustive list as other process parameters commonly used in semiconductor manufacturing may be varied.

As mentioned above, within a region, the process conditions are substantially uniform, in contrast to gradient processing techniques which rely on the inherent non-uniformity of the material deposition. That is, the embodiments, described herein locally perform the processing in a conventional manner, e.g., substantially consistent and substantially uniform, while globally over the substrate, the materials, processes, and process sequences may vary. Thus, the testing will find optimums without interference from process variation differences between processes that are meant to be the same. It should be appreciated that a region may be adjacent to another region in one embodiment or the regions may be isolated and, therefore, non-overlapping. When the regions are adjacent, there may be a slight overlap wherein the materials or precise process interactions are not known, however, a portion of the regions, normally at least 50% or more of the area, is uniform and all testing occurs within that region. Further, the potential overlap is only allowed with material of processes that will not adversely affect the result of the tests. Both types of regions are referred to herein as regions or discrete regions.

In some embodiments, the present invention discloses capacitor testing structures to evaluate dielectric materials, for example, to identify their dielectric constant values, or their leakage current characteristics. Advanced semiconductor devices can employ novel materials such as metal gate electrodes and high-k dielectrics, which comprise dielectric materials having a dielectric constant greater than that of silicon dioxide. Typically high-k dielectric materials include aluminum oxide, hafnium oxide, zirconium oxide, tantalum oxide, titanium oxide, or their alloys such as hafnium silicon oxide or zirconium silicon oxide. Metal gate materials typically comprise a refractive metal or a nitride of a refractive metal, such as titanium nitride, titanium aluminum nitride, or titanium lanthanum nitride. Different high-k dielectric materials exhibit different dielectric constants and different leakage currents, together with different integration behavior with metal gate materials, leading to the need to screen the various high-k dielectric and metal gate materials to meet device performance levels.

In some embodiments, the present invention discloses methods to form capacitor structures on a substrate using lithography patterning process with high-k dielectric and metal gate materials. In some embodiments, the present invention discloses combinatorial workflow for evaluating high-k dielectric and metal gate materials using MOSCAP designs. High productivity combinatorial processing can be a fast and economical technique for electrically screening high-k dielectric and metal gate materials to determine their proper process integration in advanced semiconductor devices, achieving improved transistor performance through the incorporation of novel high-k dielectric and metal gate materials.

Combinatorial processing can be used to produce and evaluate different materials, chemicals, processes, process and integration sequences, and techniques related to semiconductor fabrication. For example, combinatorial processing can be used to determine optimal processing parameters (e.g., power, time, reactant flow rates, temperature, etc.) of dry processing techniques such as dry etching (e.g., plasma etching, flux-based etching, reactive ion etching (RIE)) and dry deposition techniques (e.g., physical vapor deposition (PVD), chemical vapor deposition (CVD), atomic layer deposition (ALD), etc.). Combinatorial processing can be used to determine optimal processing parameters (e.g., time, concentration, temperature, stirring rate, etc.) of wet processing techniques such as wet etching, wet cleaning, rinsing, and wet deposition techniques (e.g., electroplating, electroless deposition, chemical bath deposition, etc.).

Figure 3:
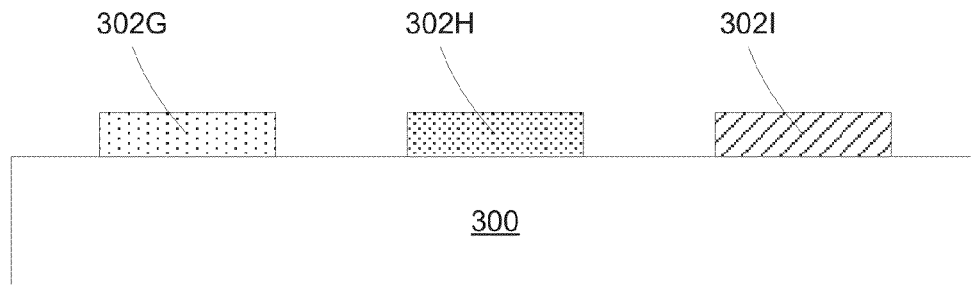
FIG. 3 illustrates a schematic diagram of a substrate that has been processed in a combinatorial manner.
Figure 3:
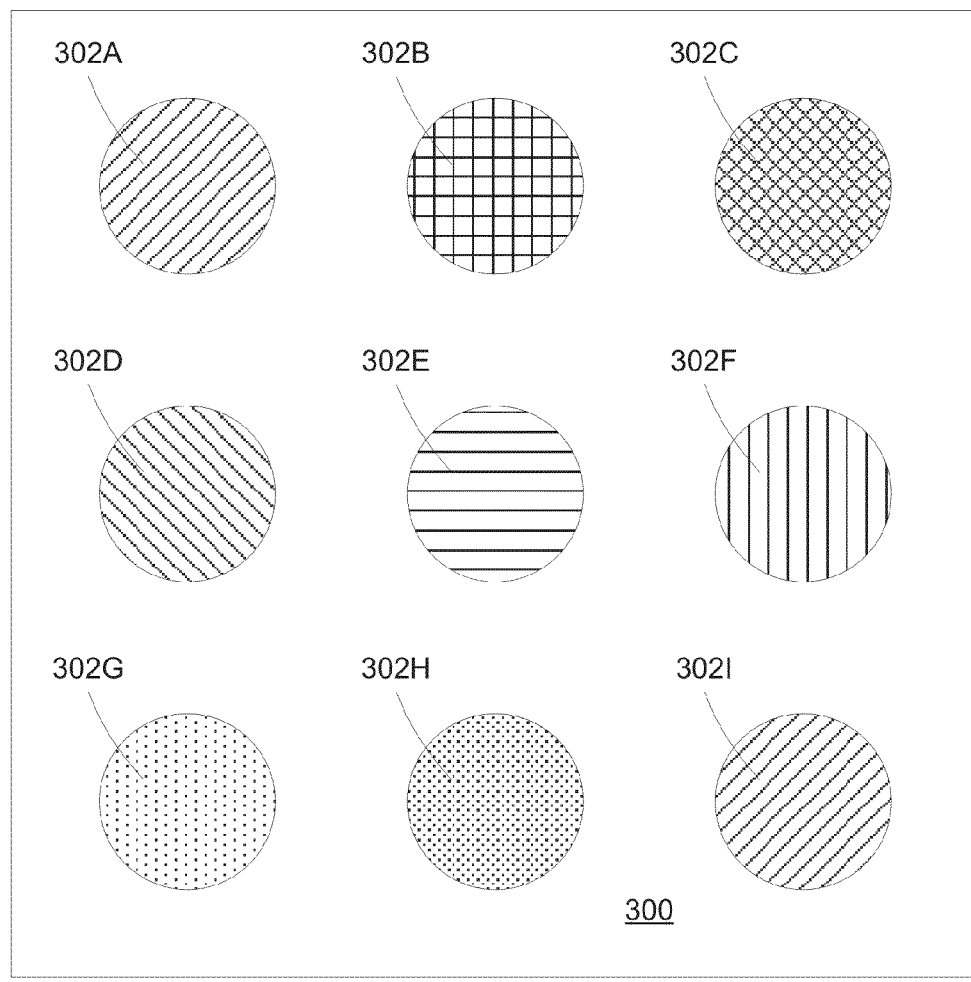

FIG. 3 illustrates a schematic diagram of a substrate that has been processed in a combinatorial manner. A substrate, 300, is shown with nine site isolated regions, 302A-302I, illustrated thereon. Although the substrate 300 is illustrated as being a generally square shape, those skilled in the art will understand that the substrate may be any useful shape such as round, rectangular, etc. The lower portion of FIG. 3 illustrates a top down view while the upper portion of FIG. 3 illustrates a cross-sectional view taken through the three site isolated regions, 302G-302I. The shading of the nine site isolated regions illustrates that the process parameters used to process these regions have been varied in a combinatorial manner. The substrate may then be processed through a next step that may be conventional or may also be a combinatorial step as discussed earlier with respect to FIG. 2.

Figure 4:
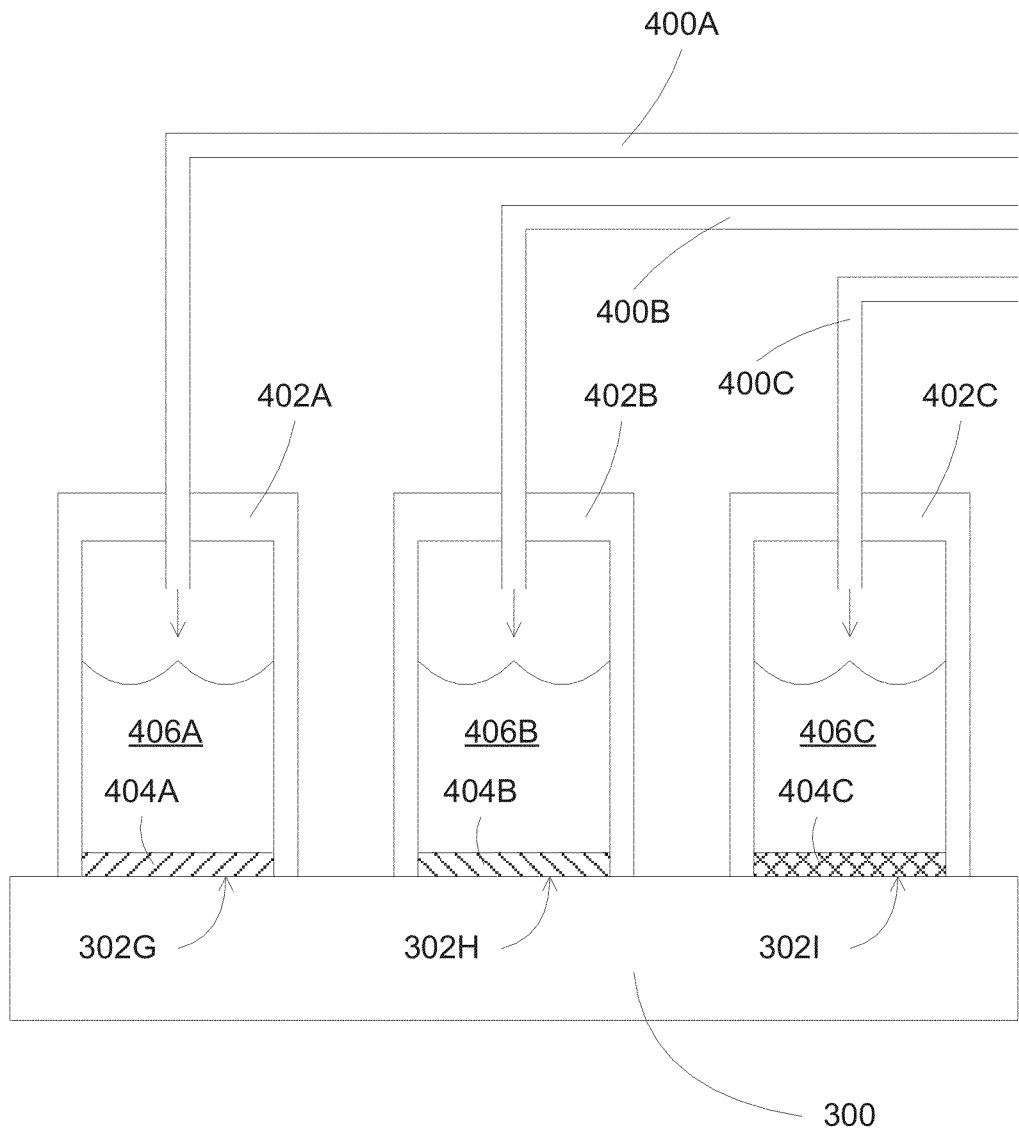
FIG. 4 illustrates a schematic diagram of a combinatorial wet processing system according to some embodiments.

FIG. 4 illustrates a schematic diagram of a combinatorial wet processing system according to some embodiments. A combinatorial wet system may be used to investigate materials deposited by solution-based techniques. An example of a combinatorial wet system is described in U.S. Pat. No. 7,544,574 cited earlier. Those skilled in the art will realize that this is only one possible configuration of a combinatorial wet system. FIG. 4 illustrates a cross-sectional view of substrate, 300, taken through the three site isolated regions, 302G-302I similar to the upper portion of FIG. 3. Solution dispensing nozzles, 400a-400c, supply different solution chemistries, 406A-406C, to chemical processing cells, 402A-402C. FIG. 4 illustrates the deposition of a layer, 404A-404C, on respective site isolated regions. Although FIG. 4 illustrates a deposition step, other solution-based processes such as cleaning, etching, surface treatment, surface functionalization, etc. may be investigated in a combinatorial manner. The solution-based treatment can be customized for each of the site isolated regions.

In some embodiments, the dielectric layer is formed through a deposition process, such as chemical vapor deposition (CVD), atomic layer deposition (ALD), or physical vapor deposition (PVD). The metal electrode layer can be formed by PVD, CVD or ALD through a shadow mask or by a lithography patterning process.

Figure 5:
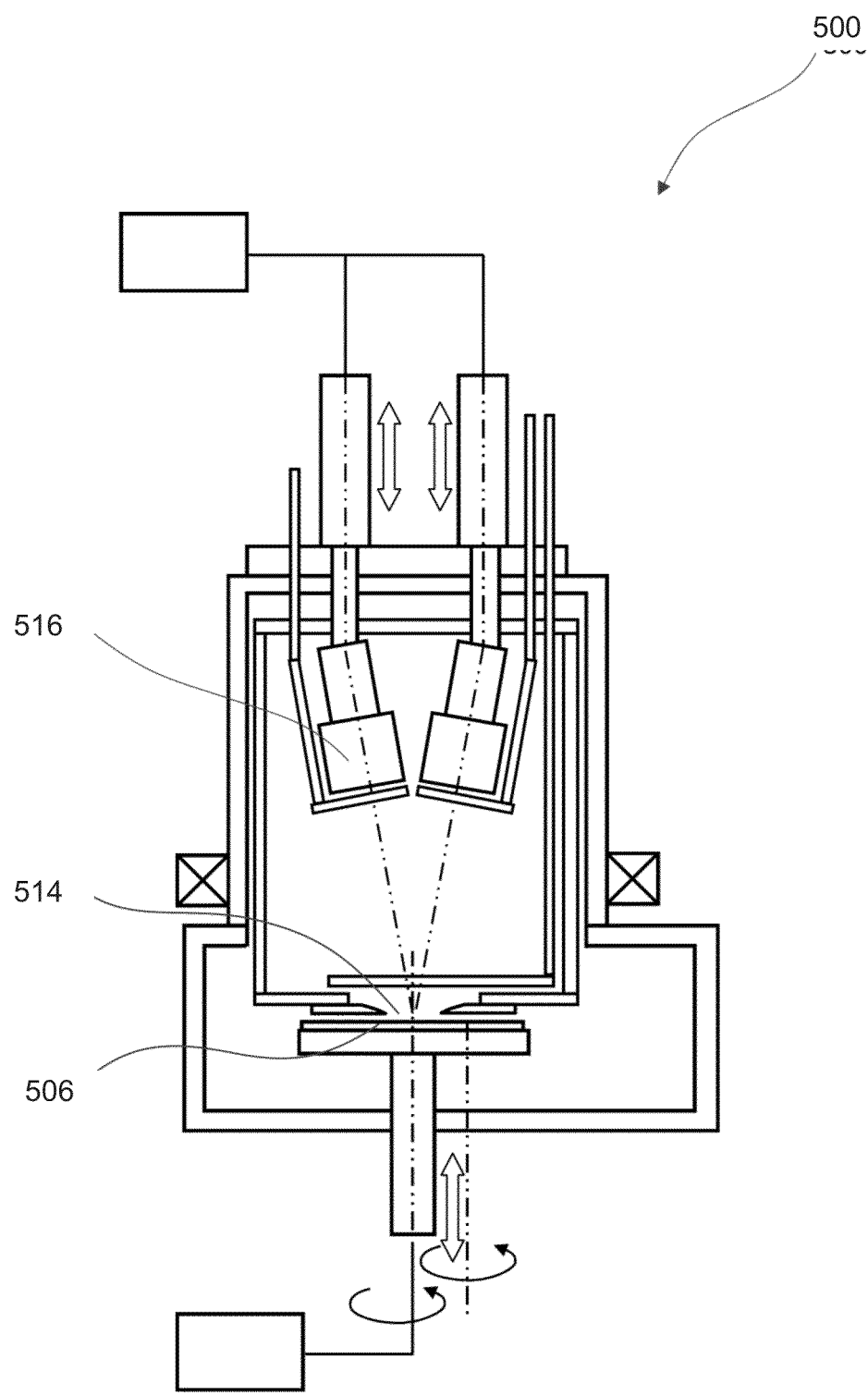
FIG. 5 illustrates a simplified schematic diagram illustrating a sputter chamber configured to perform combinatorial processing.

FIG. 5 illustrates a simplified schematic diagram illustrating a sputter chamber configured to perform combinatorial processing. The sputter system 500 generally includes a process chamber, one or more sputtering sources, and a transport system capable of positioning the substrate such that any area of the substrate can be exposed to sputtered material. The apparatus can further comprise an aperture positioned under each sputtering source, with the aperture oriented normal to the substrate and located adjacent to but not touching the substrate. The aperture typically has an opening smaller than the substrate so that discrete regions of the substrate can be subjected to distinct process conditions in a combinatorial manner. However, there is no particular limit on the size of the aperture. Typical apertures can range from a minimum of about 10 mm in one dimension, and can be square, round, or rectangular, for example. For combinatorial processing, the apertures are small enough such that films can be deposited on a plurality of site-isolated regions on a substrate. For high deposition rate sputtering to coat an entire substrate, the aperture can be up to approximately full substrate size.

The process chamber provides a controlled atmosphere so that sputtering can be performed at any gas pressure or gas composition necessary to perform the desired combinatorial processing. Typical processing gases include argon, oxygen, hydrogen, or nitrogen. However, additional gases can be used as desired for particular applications.

The transport system comprises a substrate support capable of controlling substrate temperature up to about 550 C, and applying a bias voltage of a few hundred volts.

In a sputter system 500, a plurality of sputtering sources 516 are positioned at an angle so that they can be aimed through a single aperture 514 to a site-isolated region on a substrate 506. The sputtering sources 516 are positioned about 100-300 mm from the aperture 514 to ensure uniform flux to the substrate within the site-isolated region. Details of the combinatorial PVD system are described in U.S. patent application Ser. No. 12/027,980 filed on Feb. 7, 2008 and U.S. patent application Ser. No. 12/028,643 filed on Feb. 8, 2008, which are herein incorporated by reference.

In some embodiments, a deposition process can be performed in the sputter system 500 in a combinatorial manner. The combinatorial deposition process generally includes exposing a first site-isolated region of a surface of a substrate to material from a sputtering source under a first set of process parameters, and exposing a second site-isolated region of a surface of the substrate to material from a sputtering source under a second set of process parameters. During exposure of the surface of the substrate to the sputtering source, the remaining area of the substrate is not exposed to the material from the sputtering target, enabling site-isolated deposition of sputtered material onto the substrate. The combinatorial process can further include exposing three or more site-isolated regions of the substrate to material from a sputtering source under distinct sets of process parameters. The combinatorial process can further comprise depositing additional layers onto any site-isolated region to build multi-layered structures if desired. In this manner, a plurality of process conditions to deposit one or a plurality of layers can be explored on a single substrate under distinct process parameters.

The process parameters that can be combinatorially varied generally comprise sputtering parameters, sputtering atmosphere parameters, substrate parameters, or combinations thereof. Sputtering parameters typically comprise exposure times, power, sputtering target material, target-to-substrate spacing, or a combination thereof. Sputtering atmosphere parameters typically comprise total pressure, carrier gas composition, carrier gas flow rate, reactive gas composition, reactive gas flow rate, or combinations thereof. The reactive gas flow rate can be set to greater than or equal to zero in order to vary the reactive gas composition in an inert carrier gas. The substrate parameters typically comprise substrate material, surface condition (e.g., roughness), substrate temperature, substrate bias, or combinations thereof.

Substrates can be a conventional round 200 mm, 300 mm, or any other larger or smaller substrate/wafer size. In other embodiments, substrates may be square, rectangular, or other shape. One skilled in the art will appreciate that substrate may be a blanket substrate, a coupon (e.g., partial wafer), or even a patterned substrate having predefined regions. In some embodiments, a substrate may have regions defined through the processing described herein.

Figure 6:
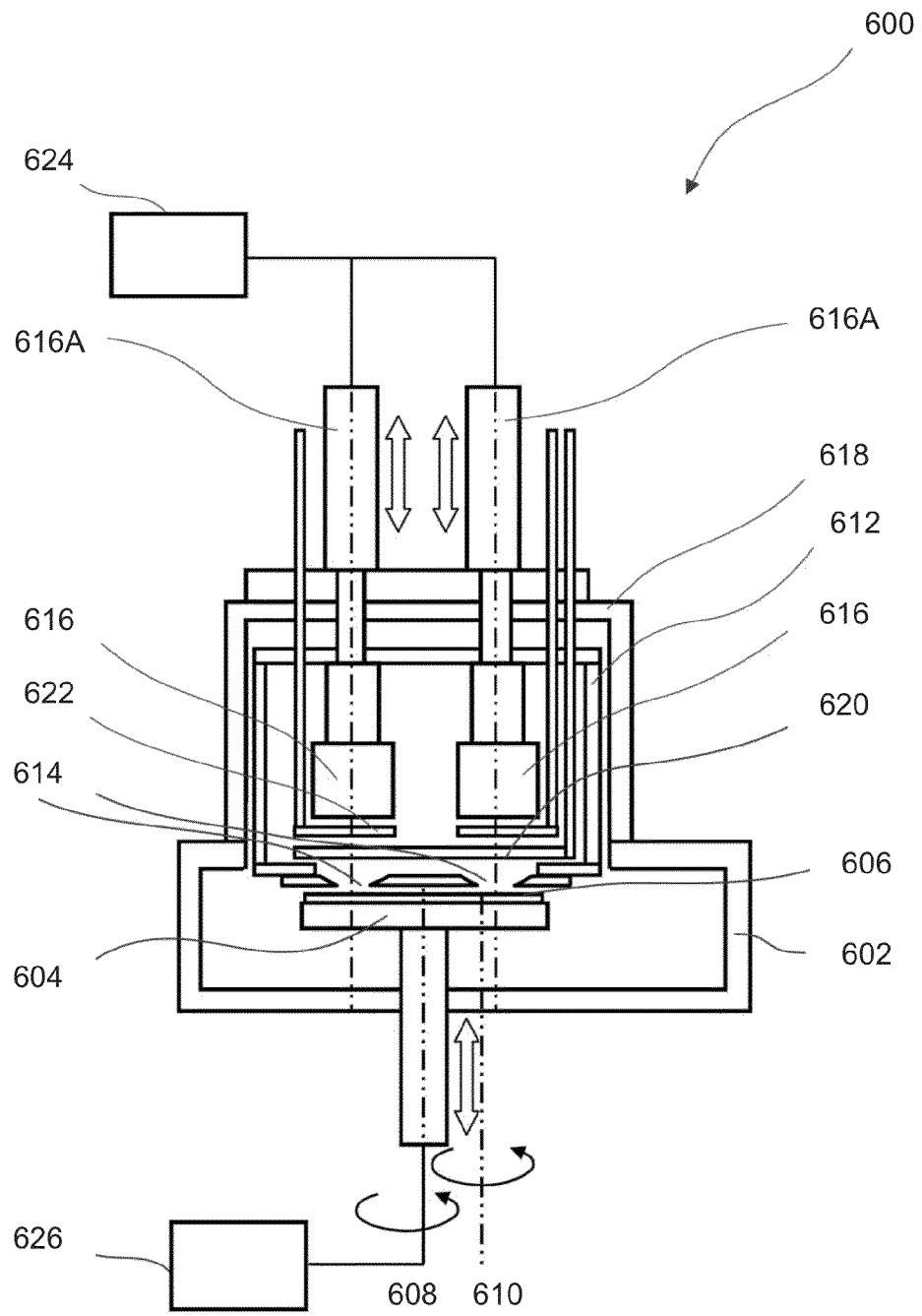
FIG. 6 is a simplified schematic diagram illustrating another sputter chamber configured to perform combinatorial processing according to some embodiments.

FIG. 6 is a simplified schematic diagram illustrating another sputter chamber configured to perform combinatorial processing according to some embodiments. Processing chamber 600 includes a bottom chamber portion 602 disposed under top chamber portion 618. Within bottom portion 602, substrate support 604 is configured to hold a substrate 606 disposed thereon and can be any known substrate support, including but not limited to a vacuum chuck, electrostatic chuck or other known mechanisms. Substrate support 604 is capable of both rotating around its own central axis 608 (referred to as "rotation" axis), and rotating around an exterior axis 610 (referred to as "revolution" axis). Such dual rotary substrate support can be useful for combinatorial processing using site-isolated mechanisms. Other substrate supports, such as an X-Y table, can also be used for site-isolated deposition. In addition, substrate support 604 may move in a vertical direction. It should be appreciated that the rotation and movement in the vertical direction may be achieved through known drive mechanisms which include magnetic drives, linear drives, worm screws, lead screws, a differentially pumped rotary feed through drive, etc. Power source 626 provides a bias power to substrate support 604 and substrate 606, and produces a bias voltage on substrate 606. Substrate 606 can be a conventional round 200 mm, 300 mm, or any other larger or smaller substrate/wafer size. In other embodiments, substrate 606 can be square, rectangular, or other suitable shape. One skilled in the art will appreciate that substrate 606 can be a blanket substrate, a coupon (e.g., partial wafer), or even a patterned substrate having predefined regions. In another embodiment, substrate 606 can have regions defined through the processing described herein.

Top chamber portion 618 of chamber 600 in FIG. 6 includes shield 612, which defines a confinement region over a radial portion of substrate 606. Shield 612 is a sleeve having a base (optionally integrated with the shield) and an optional top within chamber 600 that can be used to confine a plasma generated therein. The generated plasma dislodges atoms from a sputtering target (causing material to be ejected from the sputtering target) and the sputtered atoms are deposited on a site-isolated region of the substrate 606. Deposition can be performed in an inert gas atmosphere (e.g., an argon carrier gas) to deposit materials such as pure metals, or in the presence of reactive gases such as nitrogen or oxygen to deposit molecules such as metal oxides or metal nitrides. Neutral atoms or molecules (optionally in an excited electronic state) can be deposited. Alternatively, ions can be deposited, in which case a substrate bias voltage can be used advantageously to tune the energy of the ions arriving at the site-isolated region. Chamber pressure and gas flow rates can be adjusted to control the process; for example, the stoichiometry of layers formed in a reactive atmosphere can be tuned by adjusting the relative flow rate of the reactive gas(es).

Shield 612 is capable of being moved in and out of chamber 600, i.e., the shield is a replaceable insert. Shield 612 includes an optional top portion, sidewalls and a base. In some embodiments, shield 612 is configured in a cylindrical shape, however, the shield may be any suitable shape and is not limited to a cylindrical shape.

The base of shield 612 includes a plurality of apertures 614 in an aperture plate through which one or more site-isolated region of the surface of substrate 606 is exposed for deposition or some other suitable semiconductor processing operations. Aperture shutter 620 is moveably disposed over the base of shield 612. In some embodiments, aperture shutter 620 can be moved across a bottom surface of the base of shield 612 in order to cover or expose one or more apertures 614. Typically, only one aperture is uncovered at any one time to prevent cross-contamination between site-isolated regions. In some embodiments, aperture shutter 620 is controlled through an arm extension which moves the aperture shutter to expose or cover an aperture 614. It should be noted that although a single aperture per sputtering source is illustrated, multiple apertures may be included for each sputtering source. Each aperture can be associated with a dedicated aperture shutter or an aperture shutter can be configured to cover more than one aperture simultaneously or separately. Alternatively, aperture 614 can be a larger opening and aperture shutter 620 can extend with that opening to either completely cover the aperture or place one or more fixed apertures within that opening for processing the defined regions. The dual rotary substrate support 604 is useful to the site-isolating mechanism, and allows any location of the substrate or wafer to be placed under the aperture 614. Hence, site-isolated deposition is possible at any location on the wafer/substrate.

A sputtering source shutter, 622 can also be included. Sputtering source shutter 622 functions to seal off a deposition source when the deposition source may not be used for the processing in some embodiments. For example, two sputtering sources 616 are illustrated in FIG. 6. Sputtering sources 616 are moveable in a vertical direction so that one or both of the sources can be lifted from the slots of the shield. While two sputtering sources are illustrated, any number of sputtering sources can be included, constrained only by space limitations, e.g., one, three, four or more sputtering sources can be included. Typical embodiments for combinatorial processing can include 4 to 6 sputtering sources. Where more than one sputtering source is included, the plurality of sputtering sources may be referred to as a cluster of sputtering sources. Sputtering source shutter 622 can be moved to isolate the lifted sputtering sources from the processing area defined within shield 612. In this manner, the sputtering sources can be isolated from certain processes when desired. It should be appreciated that sputtering source shutter 622 can be integrated with the top of the shield 612 to cover the opening as the sputtering source is lifted or a sputtering source shutter 622 can be used for each site-isolated region.

Top chamber portion 618 of chamber 600 of FIG. 6 includes sidewalls and a top plate which house shield 612. Arm extensions 616a, which are fixed to sputtering sources 616 can be attached to a suitable drive, e.g., lead screw, worm gear, etc., configured to vertically move sputtering sources 616 toward or away from a top plate of top chamber portion 618. In typical use for high deposition rate sputtering, the sputtering target is positioned such that the target-to-substrate spacing is from about 20 mm to about 100 mm from the substrate, which is much closer than the typical spacing of 80-300 mm used in most sputtering systems. In some embodiments, the target-to-substrate spacing is from about 50 mm to about 75 mm. A larger spacing can reduce the deposition rate while a smaller spacing can make it difficult to strike and sustain the plasma.

Figure 7A:
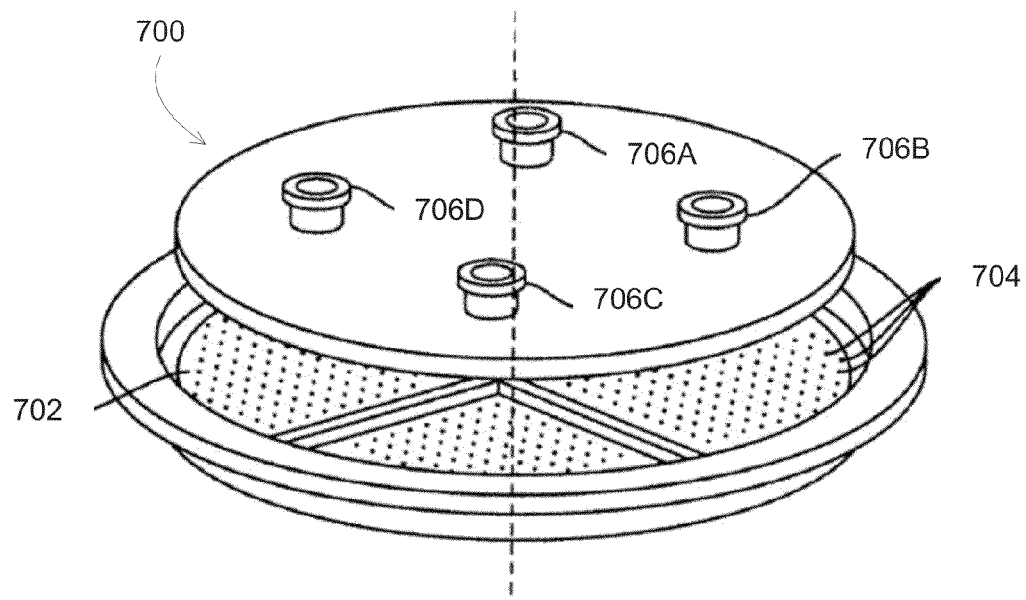
FIGS. 7A-7B illustrate examples of a large area ALD or CVD showerheads used for combinatorial processing.
Figure 7B:
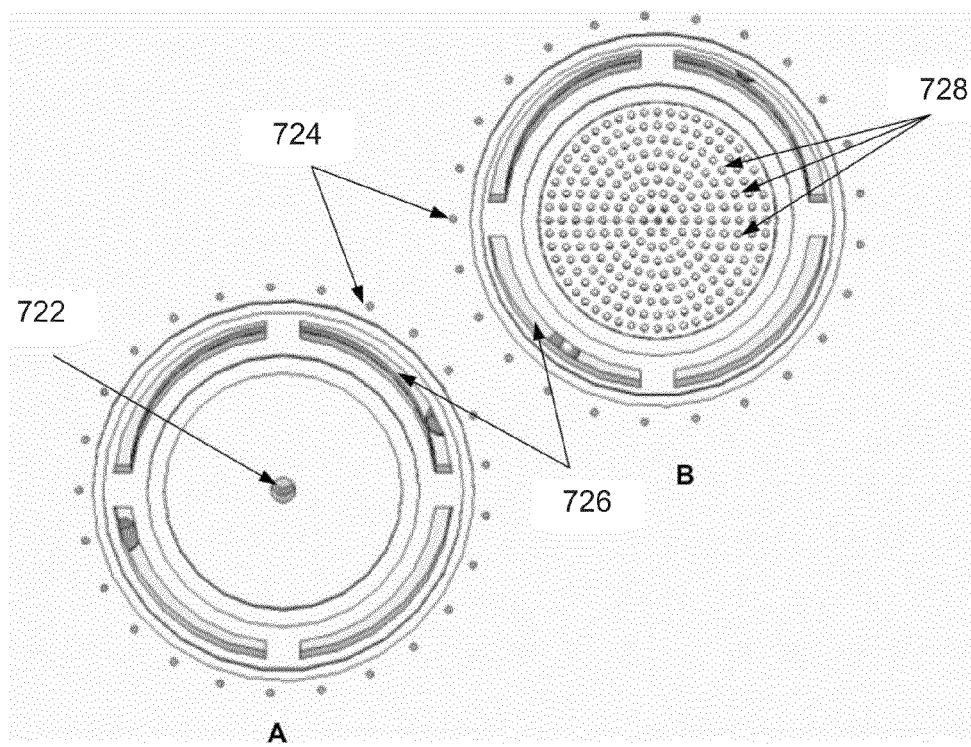

FIGS. 7A-7B illustrate examples of a large and small area ALD or CVD showerheads used for combinatorial processing. Details of large area showerhead and its use may be found in U.S. patent application Ser. No. 12/013,729 entitled "Vapor Based Combinatorial Processing" filed on Jan. 14, 2008 and claiming priority to Provisional Application No. 60/970,199 filed on Sep. 5, 2007, U.S. patent application Ser. No. 12/013,759 entitled "Vapor Based Combinatorial Processing" filed on Jan. 14, 2008 and claiming priority to Provisional Application No. 60/970,199 filed on Sep. 5, 2007, and U.S. patent application Ser. No. 12/205,578 entitled "Vapor Based Combinatorial Processing" filed on Sep. 5, 2008 which is a Continuation Application of the U.S. patent application Ser. No. 12/013,729 and claiming priority to Provisional Application No. 60/970,199 filed on Sep. 5, 2007, all of which are herein incorporated by reference. Details of small area showerhead and its use may be found in U.S. patent application Ser. No. 13/302,097 entitled "Combinatorial Deposition Based on a Spot Apparatus" filed on Nov. 22, 2011, and U.S. patent application Ser. No. 11/468,422 entitled "Combinatorial Approach for Screening of ALD Film Stacks" filed on Nov. 22, 2011, all of which are herein incorporated by reference.

The large area ALD or CVD showerhead, 700, illustrated in FIG. 7A comprises four regions, 702, used to deposit materials on a substrate. As an example, in the case of a round substrate, four different materials and/or process conditions could be used to deposit materials in each of the four quadrants of the substrate (not shown). Precursor gases, reactant gases, purge gases, etc. are introduced into each of the four regions of the showerhead through gas inlet conduits 706a-706b. For simplicity, the four regions, 702, of showerhead, 700, have been illustrated as being a single chamber. Those skilled in the art will understand that each region, 702, of showerhead, 700, may be designed to have two or more isolated gas distribution systems so that multiple reactive gases may be kept separated until they react at the substrate surface. Also for simplicity, on a single gas inlet conduit, 706a-706d, is illustrated for each of the four regions. Those skilled in the art will understand that each region, 702, of showerhead, 700, may have multiple gas inlet conduits. The gases exit each region, 702, of showerhead, 700, through holes, 704, in the bottom of the showerhead. The gases then travel to the substrate surface and react at the surface to deposit a material, etch an existing material on the surface, clean contaminants found on the surface, react with the surface to modify the surface in some way, etc. The showerhead illustrated in FIG. 7A is operable to be used with any of a CVD, PECVD, ALD, or PEALD technology.

As discussed previously, showerhead, 700, in FIG. 7A results in a deposition (or other process type) on a relatively large region of the substrate. In this example, a quadrant of the substrate. To address the limitations of the combinatorial showerhead illustrated in FIG. 7A, small spot showerheads have been designed as illustrated in FIG. 7B. FIG. 7B illustrates a bottom view of two examples of a small spot showerhead apparatus in accordance with some embodiments. The small spot showerhead configuration, A, illustrated in FIG. 7B comprises a single gas distribution port, 722, in the center of the showerhead for delivering reactive gases to the surface of the substrate. The small size of the small spot showerhead and the behavior of the technologies envisioned to use this showerhead ensure that the uniformity of the process on the substrate is adequate using the single gas distribution port. However, the small spot showerhead configuration, B, illustrated in FIG. 7B comprises a plurality of gas distribution ports, 728, for delivering reactive gases to the surface of the substrate. This configuration can be used to improve the uniformity of the process on the substrate if required.

Each small spot showerhead is surrounded by a plurality of purge holes, 724. The purge holes introduce inert purge gases (i.e. Ar, $N_2$, etc.) around the periphery of each small spot showerhead to insure that the regions under each showerhead can be processed in a site isolated manner. The gases, both the reactive gases and the purge gases, are exhausted from the process chamber through exhaust channels, 726, that surround each of the showerheads. The combination of the purge holes, 724, and the exhaust channels, 726, ensure that each region under each showerhead can be processed in a site isolated manner. The diameter of the small spot showerhead (i.e. the diameter of the purge ring) can vary between about 40 mm and about 100 mm. Advantageously, the diameter of the small spot showerhead is about 65 mm.

Using a plurality of small spot showerheads as illustrated in FIG. 7B allows a substrate to be processed in a combinatorial manner wherein different parameters can be varied as discussed above. Examples of the parameters comprise process material composition, process material amounts, reactant species, processing temperatures, processing times, processing pressures, processing flow rates, processing powers, processing reagent compositions, the rates at which the reactions are quenched, atmospheres in which the processes are conducted, an order in which materials are deposited, etc.

Figure 8:
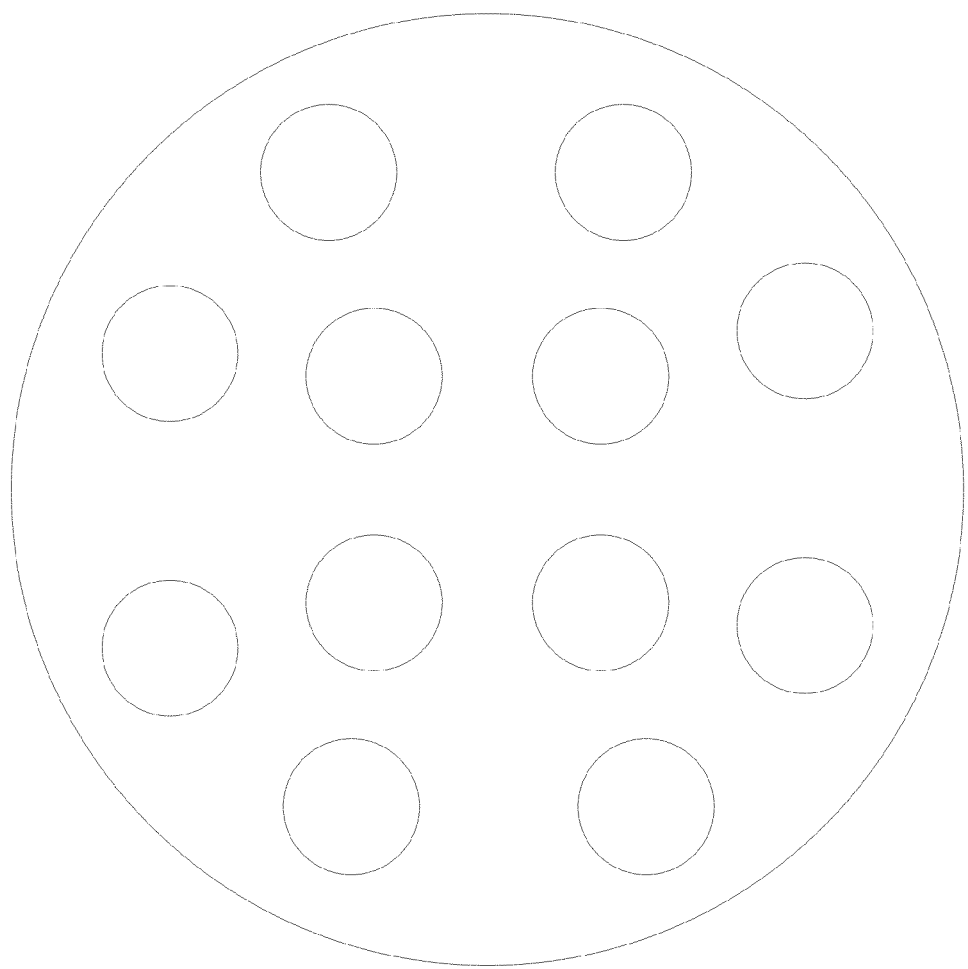
FIG. 8 illustrates one example of a pattern of site isolated regions that can be processed using a small spot showerhead apparatus in accordance with some embodiments.

FIG. 8 illustrates one example of a pattern of site isolated regions that can be processed using a small spot showerhead apparatus in accordance with some embodiments. In FIG. 8, the substrate is still generally divided into four quadrants and within each quadrant, three site isolated regions can be processed using small spot showerheads as illustrated in FIG. 7B, yielding twelve site isolated regions on the substrate. Therefore, in this example, twelve independent experiments could be performed on a single substrate.

In some embodiments, the present invention discloses electrical testing of semiconductor devices to evaluate effective work function, for example, to identify compatible and appropriate materials for a metal gate stack of PMOS (p-type metal-oxide-semiconductor) or NMOS (n-type metal-oxide-semiconductor) transistors that can satisfy the device performance. The semiconductor devices can be MOS (metal-oxide-semiconductor) capacitors, including a metal electrode disposed on a high-k dielectric on a terrace oxide on a semiconductor substrate. In some embodiments, the MOS capacitors are patterned using known lithography techniques, having active areas isolated by patterned field oxide. The patterned MOS capacitors can be free of edge defects, having the field oxide protecting the active areas during and after the device fabrication processes. The patterned MOS capacitors can be free of probing damage, having the metal probe pads separated from the active areas. The active areas can be independent of the metal areas and can be uniform across the semiconductor substrate. The evaluation can be performed for multilayer metal stacks deposited in different tools such as ALD (atomic layer deposition) or PVD (physical vapor deposition) systems. In addition, the test chip can be designed with several repetitions of the same structures in different areas of the die, so the MOSCAP workflow can tolerate significant misalignment between the lithography defined dies and the combinatorial oxide terracing and metal deposition. In the following description, MOSCAP structures are described in some embodiments, but the invention is not so limited, and can be used for evaluating any other device structures such as MOSFET (metal oxide semiconductor field effect transistor).

Advanced semiconductor devices can employ novel materials such as metal gate electrodes and high-k dielectrics, which comprise dielectric materials having a dielectric constant greater than that of silicon dioxide. Typically high-k dielectric materials include aluminum oxide, hafnium oxide, zirconium oxide, tantalum oxide, titanium oxide, or their alloys such as hafnium silicon oxide or zirconium silicon oxide. Metal gate materials typically comprise a refractory metal or a nitride of a refractory metal, such as titanium nitride, titanium aluminum nitride, or titanium lanthanum nitride. Different combinations of high-k dielectric and metal electrode materials, together with different process conditions, can exhibit different device characteristics, such as different effective work function values, and thus can require careful screening and evaluations to obtain proper materials and process conditions.

In a MOSFET, the effective work function ($\phi_{m,eff}$), i.e., the work function at the metal/high-k interface, can strongly influence the threshold voltage of the device. The effective work function of a metal is a function of its vacuum work function ($\phi_m$), i.e., the work function measured on the surface of a metal in contact with vacuum, and the properties of metal/high-k interface such as, interface states, impurity absorption, etc.

The vacuum work function of a metal can be measured by techniques such as Kelvin probe or photoelectron spectroscopy. The most common technique of the extraction of the effective work function of a metal stack, e.g., a metal electrode on a high-k dielectric layer, is the flatband voltage $V_{FB}$ effective oxide thickness method, with the flatband voltage, for example, extracted from a capacitance-voltage (CV) measurement.

The data can be extracted on the gate dielectrics of MOS devices, such as MOS capacitors or MOS transistors, with MOS capacitors generally preferred due to the short fabrication process.

An advantage of this technique is the ability to extract the effective work function at the metal/gate dielectric interface independent of the presence of charges in the gate dielectric stack. The charge profile in the gate dielectric can also be studied using this technique.

The flatband voltage $V_{FB}$ can be related to the gate dielectric total charge distribution $\rho(x)$ as followed $$V_{FB} = \Phi_{m,eff} - \Phi_s - \frac{1}{\varepsilon_{OX}} \int_0^{EOT} x\rho(x) dx$$

where $\phi_{m,eff}$ is the effective work function at the metal/high-k interface, $\phi_s$ is the work function of the substrate, $\varepsilon_{OX}$ is the dielectric constant of silicon oxide, EOT is the equivalent oxide thickness, and $\rho(x)$ is the charge distribution in the high-k dielectric layer.

Under the assumptions that, the density of interface states ($D_{it}$) is negligible, the density of bulk traps is negligible, the concentration of mobile charges are negligible, a fixed sheet charge of magnitude $Q_f$ per unit area exists at the dielectric/substrate interface, and a uniform distribution of fixed bulk charge $\rho$ per unit volume exists in the gate dielectric, the flatband voltage can be expressed as followed:

$$V_{FB} = \Phi_{m,eff} - \Phi_s - \frac{1}{\varepsilon_{OX}} Q_f EOT - \frac{1}{\varepsilon_{OX}} \rho \frac{EOT^2}{2}$$

Assuming that the fixed charges at the interface are much higher than the bulk charges ($|Q_f| \gg |\rho EOT|$), the flatband voltage can be approximate as $$V_{FB} = \Phi_{m,eff} - \Phi_s - \frac{1}{\varepsilon_{OX}} Q_f EOT$$

Thus the flatband band voltage $V_{FB}$ is linearly related to the effective oxide thickness EOT. When multiple flatband voltages are plotted for different equivalent oxide thickness, the effective work function $\phi_{m,eff}$ can be calculated from the intercept of the $V_{FB}$–EOT linear curve.

Different EOT can be obtained by fabricating MOS devices having the same metal gate electrode and substrate and the same gate dielectric (i.e., same $\phi_{m,eff}$ and $\phi_s$) but with different thicknesses.

However, when varying the thickness of the high-k dielectric, there can be different bulk charges in the dielectric, which can shift the flatband voltage $V_{FB}$. In addition, different high-k dielectric thicknesses can form different levels of interfacial silicon oxide, making it difficult to maintain a constant fixed charge at the interface of the silicon substrate and the high-k dielectric layer.

A more accurate methodology for effective work function extraction can be realized by a terraced oxide method. Silicon oxide layers of different thicknesses can be thermally grown on a single substrate, followed by a high-k dielectric layer and metal electrode. For terraced oxide device structures, the flatband voltage can be approximated as a linear function of the effective oxide thickness, using a three-charge model, for example, the interface charge between the substrate and the silicon oxide terraced layer, the interface charge between the silicon oxide terraced layer and the high-k dielectric layer, and the interface charge between the high-k dielectric layer and the metal electrode.

In the terraced oxide method, the constant interface fixed charge between the silicon oxide and the silicon substrate can be maintained, and the high-k bulk charges can also be constant due to a single thickness of the high-k layer.

In some embodiments, the present invention discloses methods to evaluate potential impact of various metal gate stacks on transistor performance and reliability, including electrical testing of metal oxide semiconductor (MOS) capacitor structures. MOS capacitor structures can be quickly and economically fabricated, permitting evaluating potential device characteristics, such as effective work function, of various materials and process conditions with fast turnaround times. For example, flatband voltage measurements can provide information directly related to the performance of high-k dielectric, such as the presence of fixed charges, mobile charges or surface state charges in the high-k or at the high-k dielectric/semiconductor interface. Effective work function extraction can provide information on the threshold voltage of the metal/high-k gate stacks.

Figure 9:
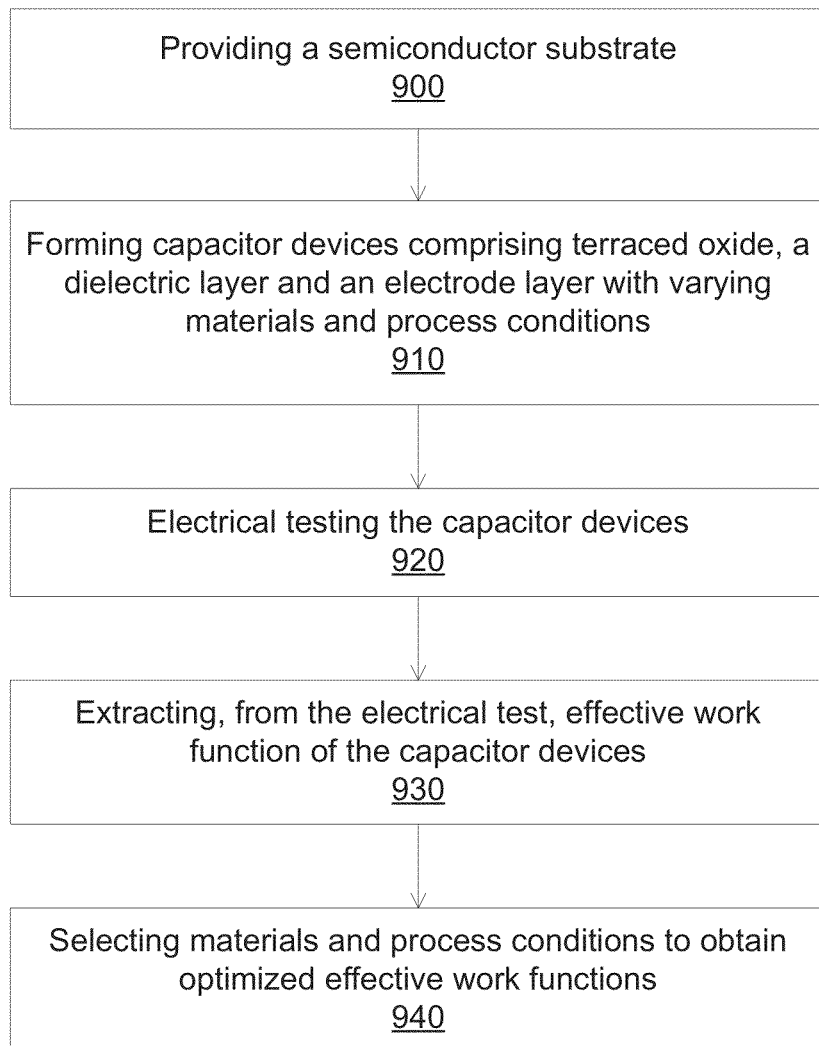
FIG. 9 illustrates an illustrative flowchart for screening metal gate stacks according to some embodiments.

FIG. 9 illustrates a flowchart for screening metal gate stacks according to some embodiments. Different high-k dielectric materials, different metal materials, and/or different process conditions such as PVD or ALD deposition for the metal electrodes can be used to fabricate MOS capacitor structures, representing gate stacks of a transistor device. The electrical performance of the MOS capacitor devices can provide the effective work function of the metal gate stacks, permitting a quick ranking of various materials and process conditions. Poor performance high-k and metal combinations, together with sub-optimum process conditions can be identified and removed without the need to fabricate and test fully-operational devices.

In operation 900, a semiconductor substrate is provided. The semiconductor substrate can be a silicon-containing substrate, a germanium-containing substrate, an III-V or II-VI substrate, or any other substrate containing a semiconductor element. In operation 910, capacitor structures are fabricated, including forming a terraced oxide on the semiconductor substrate, a high-k dielectric layer on the terraced oxide, and a metal electrode layer on the dielectric layer. The terraced oxide can include high quality silicon oxide, such as thermally grown silicon oxide. The high-k dielectric layer can include a high-k dielectric material, such as aluminum oxide, hafnium oxide, zirconium oxide, tantalum oxide, titanium oxide, or their alloys such as hafnium silicon oxide or zirconium silicon oxide. The electrode layer can include a refractive metal or a nitride of a refractive metal, such as titanium nitride, titanium aluminum nitride, or titanium lanthanum nitride.

In some embodiments, multiple site isolation regions are processed on a substrate, with varying materials and process conditions for the different site isolated regions. In some embodiments, patterned capacitor device structures are fabricated, including lithographically defined active areas, and lithographically defined metal electrodes, aligned with the active areas.

In operation 920, the capacitor devices, including an electrode disposed on a dielectric layer on a terraced oxide layer on the semiconductor substrate, are electrically tested. The electrical tests can comprise a flatband voltage measurement, for example, to determine the presence of charges in the dielectric and at the dielectric/semiconductor interface. The electrical tests can comprise I-V and C-V measurements, including single curve or cycling testing, with varying sweep voltage range, sweep speed, or sweep frequency, which can offer possible correlation to the defect states.

In operation 930, data related to the performance of the capacitor device is extracted from the electrical test. For example, effective work function of the metal/high-k electrode stack can be extracted from the electrical tests. In operation 940, high-k materials, metal electrode materials and process conditions are selected based on a comparison of the device performance.

In some embodiments, the electrical testing of MOS devices can offer a list of process compatibility between multiple high-k and metal materials and process conditions of the devices, such as the deposition techniques of the high-k layer or the metal gate layer. This list can enable the optimum device fabrication process, at least with respect to the metal gate stack in a transistor device.

In some embodiments, the present invention discloses multiple variations of the metal gate stack in the capacitor devices. For example, the capacitor devices can include different thicknesses of the terraced oxide. The capacitor devices can include different materials or process conditions of the high-k dielectric. The capacitor devices can include different materials or process conditions of the metal electrode. Other process conditions can also included, such as anneal conditions for the metal electrode layer.

Figure 10A:
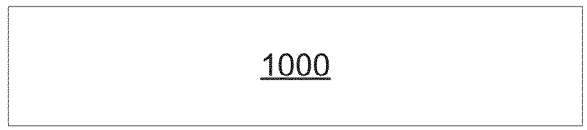
FIGS. 10A-10K illustrate illustrative cross sections of a fabrication sequence of a capacitor device for electrical testing according to some embodiments.
Figure 10B:
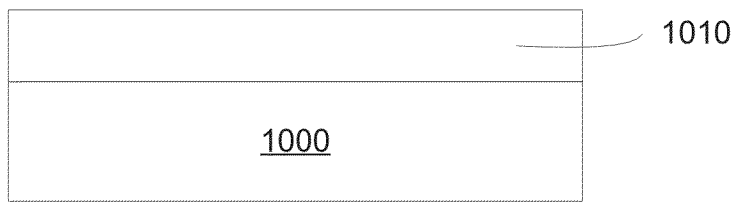

FIGS. 10A-10K illustrate illustrative cross sections of a fabrication sequence of a capacitor device for electrical testing according to some embodiments. In FIG. 10A, a semiconductor substrate 1000 is provided. In FIG. 10B, a field oxide 1010 is formed on the substrate, for example, by chemical vapor deposition (CVD) or thermally grown process. The thickness of the field oxide is about 100 nm, and can serve as an isolation material for the capacitor devices.

Figure 10C:
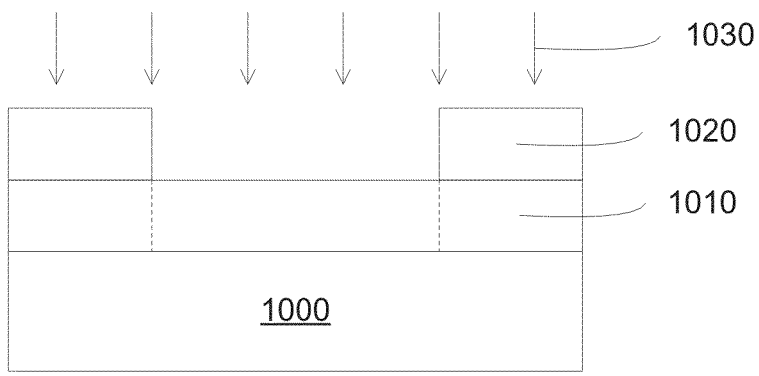

In FIG. 10C, the field oxide layer 1010 is patterned to form active areas 1017. Lithography process can be used, for example, by coating the field oxide layer 1010 with a photoresist layer 1020. After exposing the photoresist layer 1020 to a light exposure through a mask, the photoresist layer 1020 forms an image of the mask pattern. An etch process 1030, for example, a plasma etch or a wet etch, can be preformed to remove the portion of the field oxide that is not protected by the photoresist 1020.

Figure 10D:
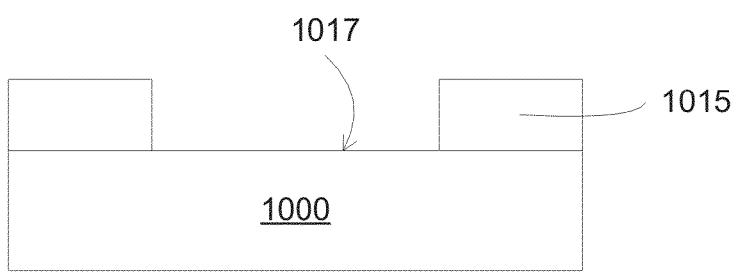

In FIG. 10D, the photoresist layer 1020 is removed, and the mask pattern is transferred to the field oxide 1015. The etched portions of the field oxide 1015 form the active areas 1017, including an exposed surface of the substrate, protected by the remaining field oxide 1015.

Figure 10E:
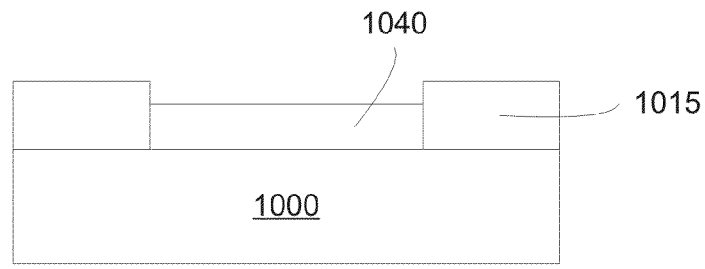

In FIG. 10E, a first oxide layer 1040 is formed in the active area. The first oxide layer can be formed by thermal oxidation, for example, to have high quality oxide interface with the silicon substrate 1000.

Figure 10F:
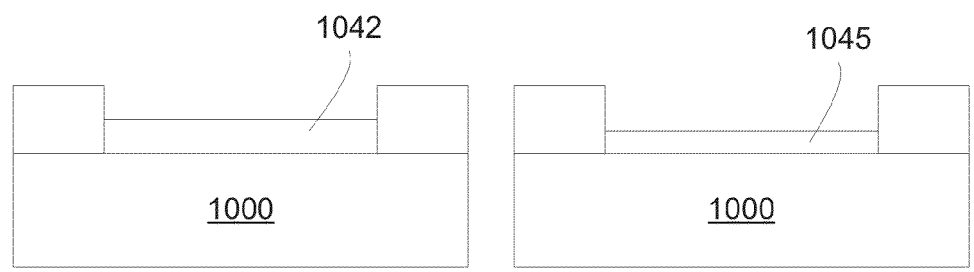

In FIG. 10F, the first oxide layer 1040 is etched, for example, in a combinatorial manner in multiple site isolated regions, to form terraced oxide layers 1042 and 1045 with different thicknesses.

Figure 10G:
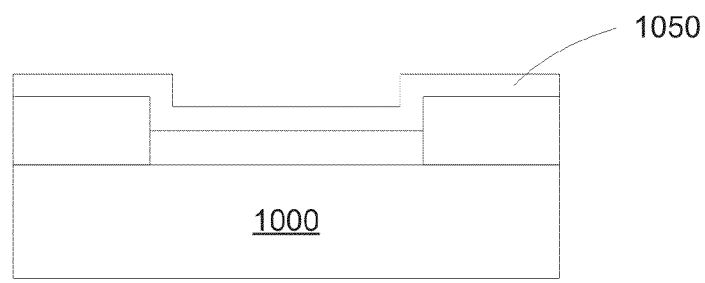

In FIG. 10G, a high-k dielectric layer 1050 is formed on the terraced oxide layers 1042 and 1045, for example, by chemical vapor deposition (CVD), or by atomic layer deposition (ALD). Various dielectric materials can be used, for example, high-k dielectric materials or composite layer of silicon dioxide and high-k material.

Figure 10H:
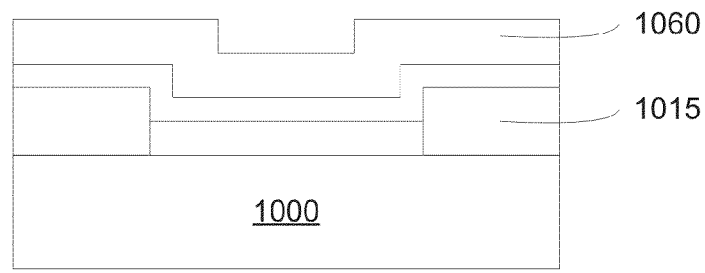

In FIG. 10H, metal electrode layer 1060 is formed on the dielectric layer 1050, for example, by physical vapor deposition (PVD), chemical vapor deposition (CVD), or by atomic layer deposition (ALD). Various metal alloy materials can be used, for example, metal nitride materials or composite layer of metal electrode layer and polysilicon conductor layer.

Figure 10I:
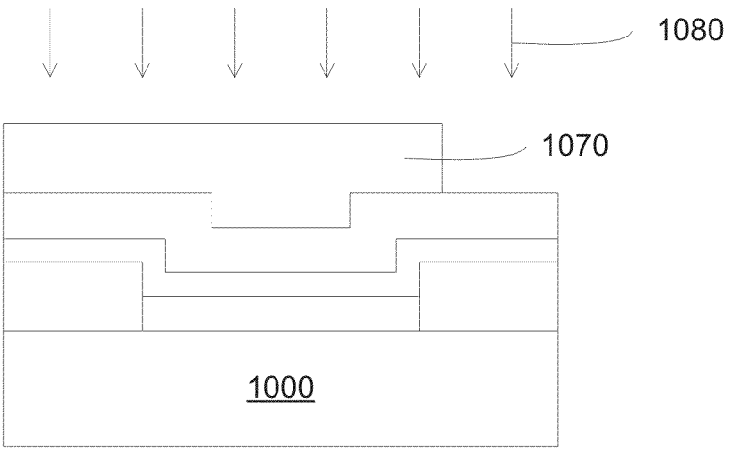

In FIG. 10I, the metal electrode layer 1060 is patterned, aligned with the active areas 1017, to form metal electrodes. Lithography process can be used, for example, by coating the metal electrode layer 1060 with a photoresist layer 1070. After exposing the photoresist layer 1070 to a light exposure through a mask, the photoresist layer 1070 forms an image of the mask pattern. An etch process 1080, for example, a plasma etch or a wet etch, can be preformed to remove the portion of the metal electrode layer that is not protected by the photoresist 1070.

Figure 10J:
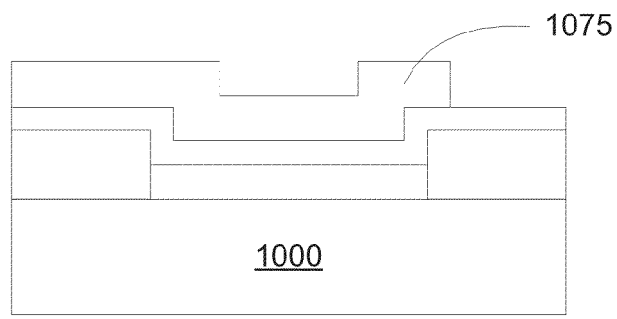

In FIG. 10J, the photoresist layer 1070 is removed, and the mask pattern is transferred to the metal electrode layer to form metal electrodes 1075. The metal electrode 1075, the high-k dielectric layer 1050, the terraced oxide layer, for example terraced oxide 1042, and the silicon substrate 1000 form a MOS capacitor device.

Figure 10K:
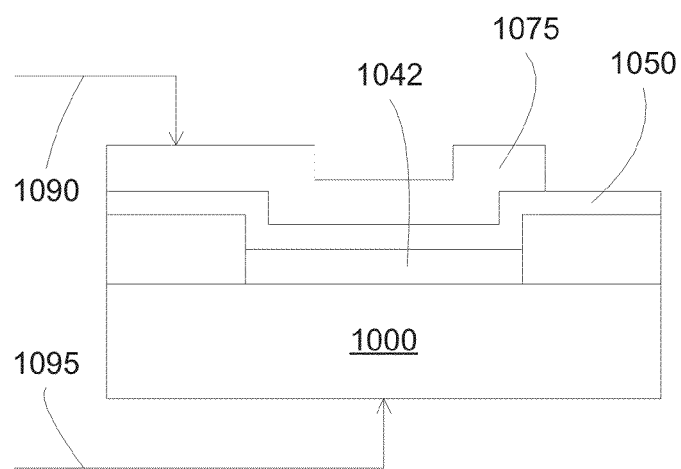

In FIG. 10K, the MOS capacitor device can be electrically tested, for example, by probing the metal electrode 1075 with top probe 1090 and the substrate 1000 with bottom probe 1095.

Figure 11:
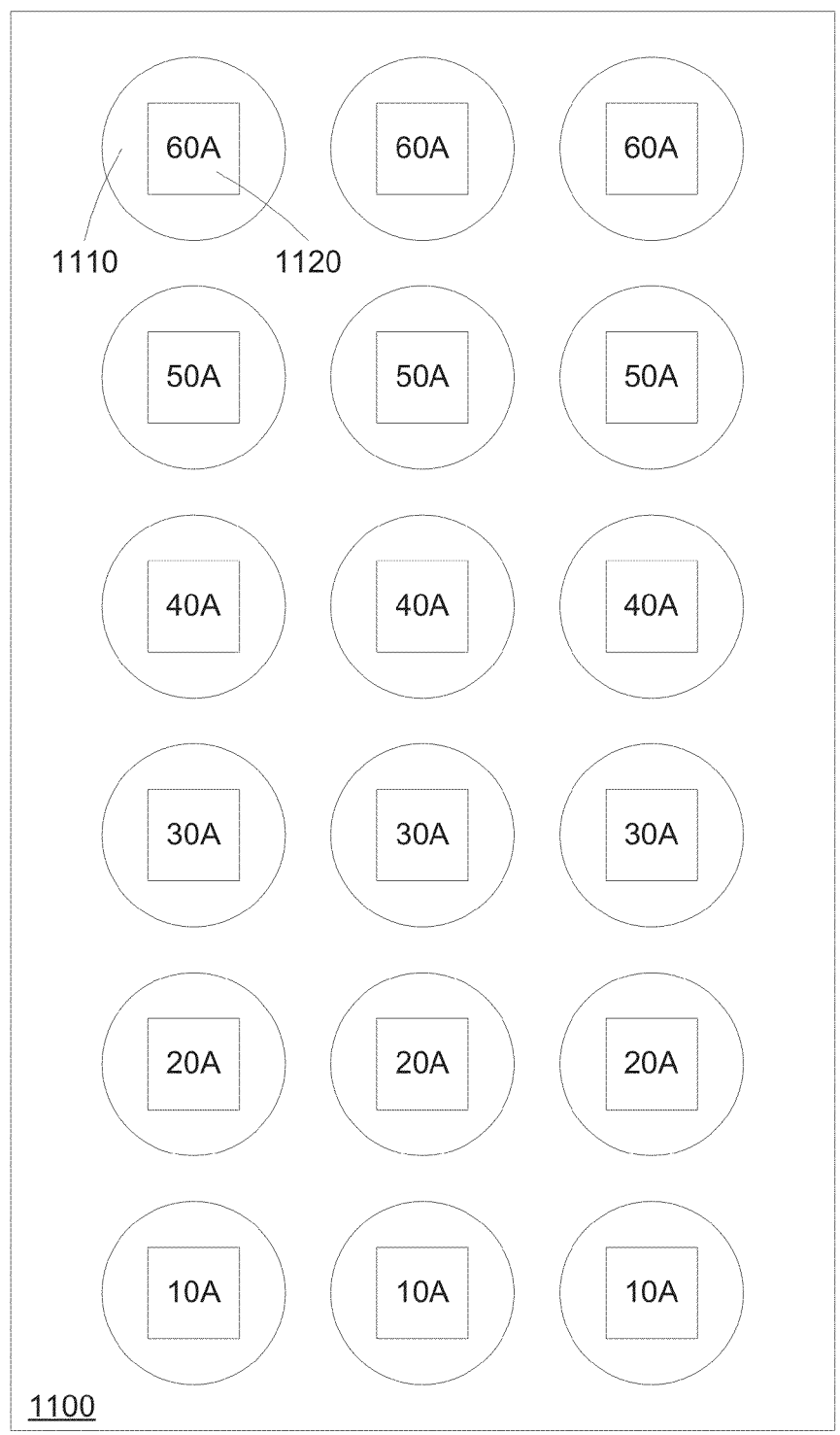
FIG. 11 illustrates an example of substrate having multiple site isolated regions containing capacitor structures fabricated thereon according to some embodiments.

FIG. 11 illustrates an example of substrate having multiple site isolated regions containing capacitor structures fabricated thereon according to some embodiments. Multiple site isolated regions 1110 are separately processed on substrate 1100. Each site isolated region can include a die 1120, which can include multiple capacitor structures. In each site isolated region, different thicknesses of the terraced oxide can be processed, for example, from 1 nm to 6 nm terraced oxide thickness. In addition, multiple site isolated regions can have a same terraced oxide thickness, for example, to allow variations of other parameters, such as the metal electrode materials. Each die 1120 can contain different capacitor sizes, for example, 1 µm×1 µm, 4 µm×4 µm, 8 µm×8 µm, 20 µm×20 µm, 100 µm×100 µm, 200 µm×200 µm, and 500 µm×500 µm. Other capacitor structures can be included, such as finger structures.

In some embodiments, the die 1120 is repeated in each site isolated regions. Different types of capacitor structures can be placed in different areas of the die, for example, as mitigation against photolithography misalignment at metal deposition and wet etch step.

Figure 12:
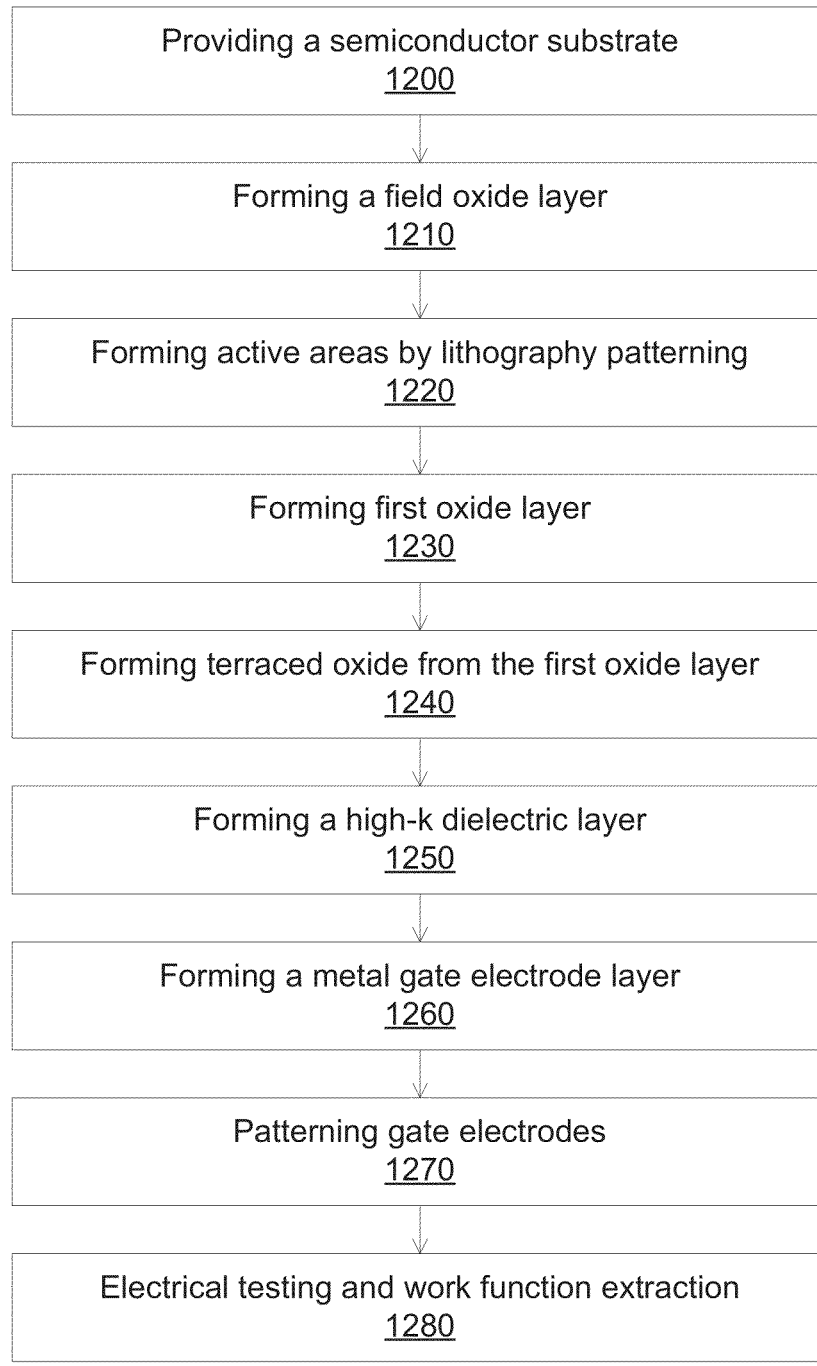
FIG. 12 illustrates an illustrative flowchart for screening metal gate stacks according to some embodiments.

FIG. 12 illustrates a flowchart for screening metal gate stacks according to some embodiments. The metal gate stack can be included in a capacitor structure with terraced oxide, high-k dielectric and metal electrode, fabricated using photolithography process. The screening process can include effective work function extraction from the capacitor structures, evaluating the feasibility of different metal gate stack materials and processes.

In operation 1200, a semiconductor substrate is provided. In operation 1210, a field oxide is formed on the substrate, for example, by thermally growth oxide or by deposition. In operation 1220, active areas of the capacitor structures are formed by photolithography, for example, by spin coating a photoresist layer, photo exposing the photoresist under a mask reticle, developing the exposed photoresist, and wet etching the exposed portion of the field oxide.

In operation 1230, a first oxide layer is formed in the active areas, for example, by thermally growing an oxide layer on the silicon substrate. In operation 1240, the first oxide layer is combinatorially wet etched to form terraced oxide of different thicknesses in different site isolated regions.

In operation 1250, a high-k dielectric layer is formed on the terraced oxide, for example, a hafnium oxide layer deposited by an ALD process. In some embodiments, the high-k dielectric layer can be formed in a combinatorial manner across the multiple site isolated regions, for example, with changing in deposition conditions or high-k materials.

In operation 1260, a metal electrode layer is formed on the high-k dielectric layer, for example, by an ALD or a PVD process. In some embodiments, the metal electrode layer can be formed in a combinatorial manner across the multiple site isolated regions, for example, with changing in deposition conditions or materials.

In operation 1270, metal electrodes of the capacitor structures are formed by photolithography, for example, by spin coating a photoresist layer, photo exposing the photoresist under a mask reticle, developing the exposed photoresist, and etching the exposed portion of the metal electrode layer. The mask reticle can be aligned with the previous pattern of the active areas so that the metal electrodes can cover the active areas to form capacitor structures.

In operation 1280, electrical testing and effective work function extraction are performed on the capacitor structures. Optional processing steps can be added, such as a rapid thermal annealing after deposition of the metal electrode layer, and a post metallization anneal with forming gas after completing the capacitor structures. In some embodiments, other test devices can be fabricated, such as transistor structures.

In some embodiments, the present invention discloses combinatorial workflow for evaluating effective work function from gate stacks, to provide optimized process conditions for gate stack formation, such as for metal gate stack using high-k dielectrics. High productivity combinatorial processing can be a fast and economical technique for electrically screening materials and process conditions to determine their suitability and possible side effects on the transistor performance, avoiding potentially costly device process development through proper selection of high-k and metal electrode materials and fabrication processes.

In some embodiments, the electrical testing comprises at least one of an I-V measurement, a C-V measurement, a flatband voltage shift measurement, or an effective work function measurement.

Figure 13:
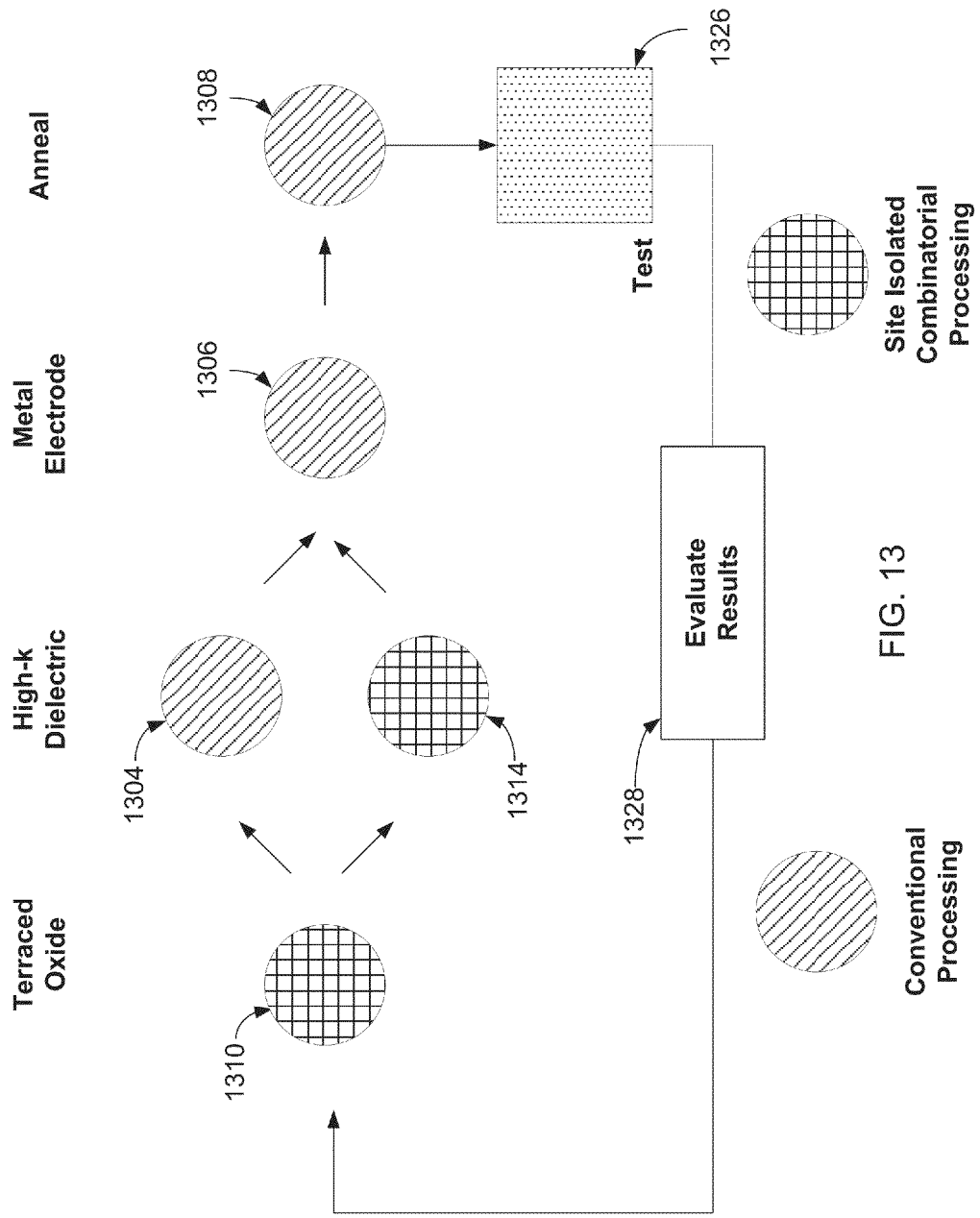
FIG. 13 illustrates a flow diagram for forming simple test structures according to an embodiment described herein.

FIG. 13 illustrates a flow diagram for forming simple test structures according to an embodiment described herein. As discussed in relation to FIG. 2, several of the layers or process steps provide opportunities to apply combinatorial techniques to the development and investigation of the materials and treatments for the layers. For evaluating gate stacks through effective work function calculation, parameter candidates include the high-k dielectric layer and the metal electrode layer. As mentioned previously, examples of suitable high-k dielectric layers comprise hafnium oxide, zirconium oxide, aluminum oxide, or any mixture combination, etc. hafnium oxide and hafnium silicon oxide are the material most often used currently as the high-k dielectric layer for metal gate stack devices. The high-k dielectric layer may be deposited using chemical vapor deposition (CVD), atomic layer deposition (ALD), or plasma enhanced CVD or ALD. These are meant to be illustrative parameters and those skilled in the art will be able to apply HPC techniques to any of the commonly used process parameters.

A process step that may be investigated using HPC techniques includes the terraced oxide formation. The terraced oxide formation is designed to facilitate the extraction of effective work function from the capacitor structures. The terraced oxide formation may be provided using HPC techniques by varying process parameters such as terraced oxide thicknesses.

Another layer that may be investigated using HPC techniques includes the metal gate electrode layer. Examples of suitable metal gate electrode materials comprise titanium, tantalum, aluminum, lanthanum, their alloys, nitrides and nitride alloys, etc. Typically, PVD is the preferred method of deposition for the metal gate electrode layer. The deposition of the metal electrode layer by PVD may be investigated using HPC techniques by varying process parameters such as material, power, pressure, target to substrate distance, atomic ratio, etc. These are meant to be illustrative parameters and those skilled in the art will be able to apply HPC techniques to any of the commonly used process parameters.

Returning to FIG. 13, through the use of a combination of conventional and combinatorial processing systems (i.e. systems capable of processing multiple isolated regions on a single substrate) a number of trajectories through the various systems illustrated in the flow diagram of FIG. 13 can be envisioned. In FIG. 13, the terraced oxide may be wet etched in a combinatorial processing manner, 1310. As discussed previously, the high-k dielectric layer may be formed in a conventional processing manner, 1304, or in a site isolated combinatorial processing manner, 1314. The metal electrode layer may be deposited in a conventional processing manner, 1306, in some embodiments where the metal electrode is not a variable. The anneal process, such as a post metallization anneal in forming gas, may be processed in a conventional processing manner, 1308. After the deposition of the various layers and subsequent processing, the various MOS capacitor devices represented by each of the site isolated regions may be testing in step 1326, and the results evaluated in step, 1328. As discussed previously, the results will form the basis for additional cycles of investigation through HPC techniques to identify materials and process conditions that evaluate the suitability of photoresist strip exposure in devices having the given high-k dielectric and metal gate electrode.

Using the simple diagram in FIG. 13, there are two possible trajectories through the process sequence, which encompass all of the possible combinations of conventional and combinatorial processing illustrated. Those skilled in the art will understand that HPC techniques may be applied to other processes not illustrated such as anneal treatments, cleaning, etching, rinsing, surface treatments, surface functionalization, etc. As more variable process steps are included, the total number of required experiments increases dramatically. This illustrates the benefits of using HPC techniques to limit the number of substrates to a manageable number and minimize the cost of the development program.

The illustrated simple diagram represents a possible evaluation process for the effects of various high-k dielectrics on a specific metal gate stack. The variables further include other process windows, such as the deposition temperature, and time.

Figure 14:
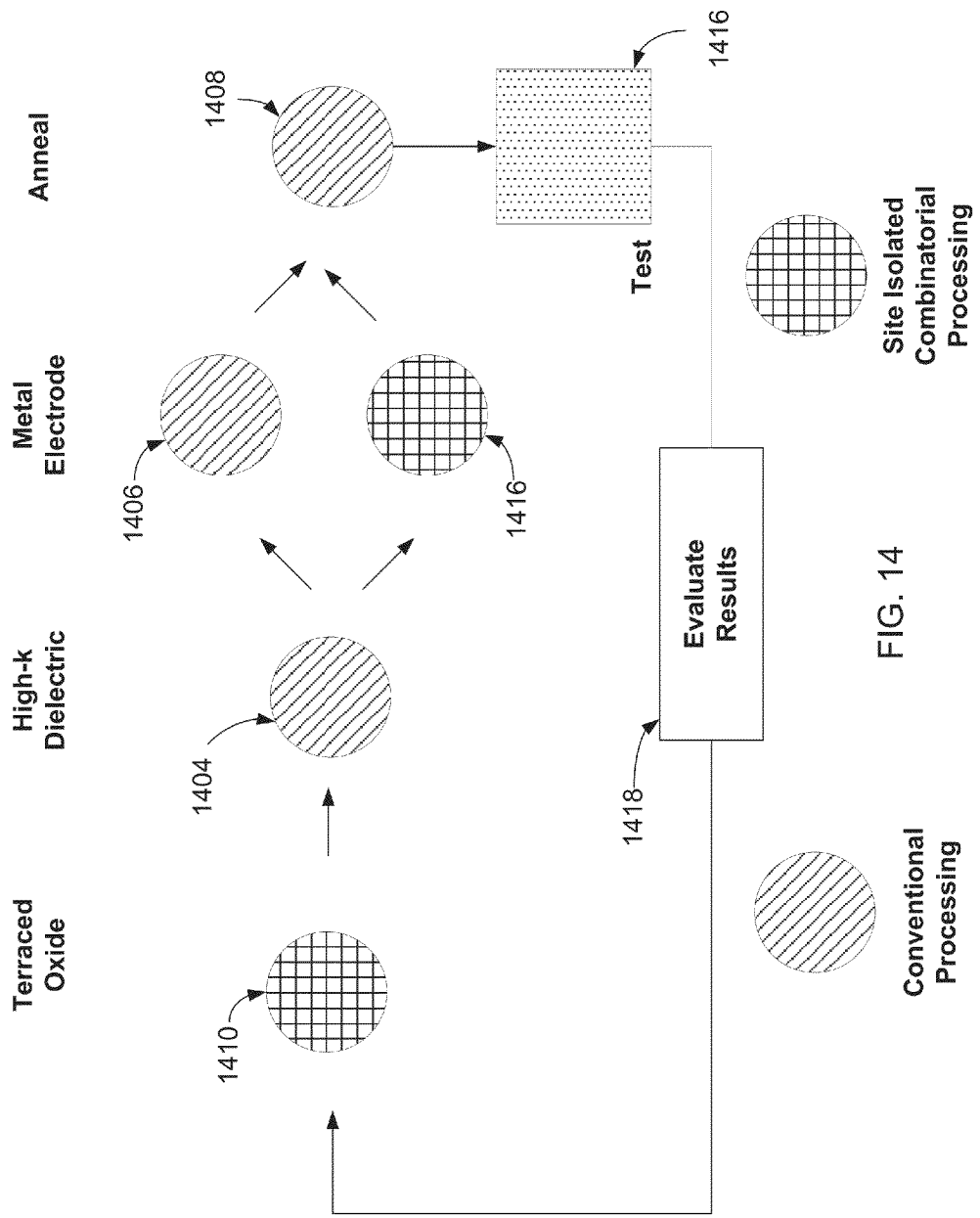
FIG. 14 illustrates a flow diagram for forming another test structure evaluation according to some embodiments.

FIG. 14 illustrates a flow diagram for forming another test structure evaluation according to some embodiments. Additional layers can be included in the test methodology, including the metal gate electrode layer. Through the use of a combination of conventional and combinatorial processing systems (i.e. systems capable of processing multiple isolated regions on a single substrate) a number of trajectories through the various systems illustrated in the flow diagram of FIG. 14 can be envisioned. In FIG. 14, the terraced oxide layer may be wet etched in a combinatorial processing manner, 1410. The high-k dielectric layer may be deposited in a conventional processing manner, 1404, in some embodiments where the high-k dielectric layer is not a variable. The metal electrode layer may be deposited in a conventional processing manner, 1406, or in a site isolated combinatorial processing manner, 1416. The anneal process, such as a post metallization anneal in forming gas, may be processed in a conventional processing manner, 1408. After the deposition of the various layers and subsequent processing, the various MOS capacitor devices represented by each of the site isolated regions may be testing in step 1426, and the results evaluated in step, 1428. As discussed previously, the results will form the basis for additional cycles of investigation through HPC techniques to identify materials and process conditions that evaluate the suitability of photoresist strip exposure with respect to different metal gate electrode in devices having the given high-k dielectric.

Using the simple diagram in FIG. 14, there are two possible trajectories through the process sequence. These two trajectories encompass all of the possible combinations of conventional and combinatorial processing illustrated. Those skilled in the art will understand that HPC techniques may be applied to other processes not illustrated such as anneal treatments, cleaning, rinsing, etching, surface treatments, surface functionalization, etc. As more variable process steps are included, the total number of required experiments increases dramatically. This illustrates the benefits of using HPC techniques to limit the number of substrates to a manageable number and minimize the cost of the development program.

Figure 15:
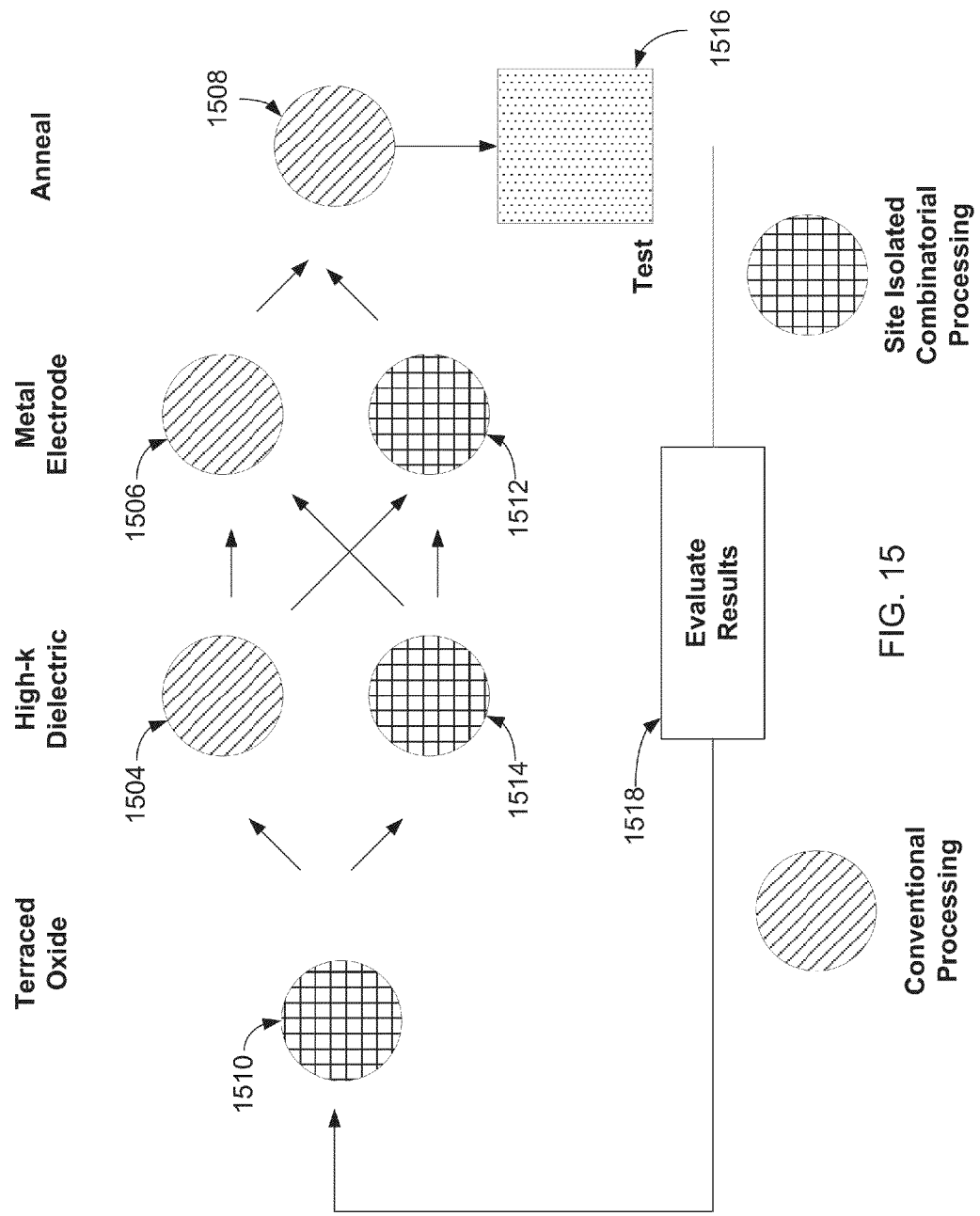
FIG. 15 illustrates a flow diagram for forming another test structure evaluation according to some embodiments.

FIG. 15 illustrates a flow diagram for forming another test structure evaluation according to some embodiments. Additional layers can be included in the test methodology, including the metal gate electrode layer and the high-k dielectric. Through the use of a combination of conventional and combinatorial processing systems (i.e. systems capable of processing multiple isolated regions on a single substrate) a number of trajectories through the various systems illustrated in the flow diagram of FIG. 15 can be envisioned. In FIG. 15, the terraced oxide layer may be wet etched in a combinatorial processing manner, 1510. The high-k dielectric layer may be deposited in a conventional processing manner, 1504, or in a site isolated combinatorial processing manner, 1514. The metal electrode layer may be deposited in a conventional processing manner, 1506, or in a site isolated combinatorial processing manner, 1516. The anneal process, such as a post metallization anneal in forming gas, may be processed in a conventional processing manner, 1508. After the deposition of the various layers and subsequent processing, the various MOS capacitor devices represented by each of the site isolated regions may be testing in step 1526, and the results evaluated in step, 1528. As discussed previously, the results will form the basis for additional cycles of investigation through HPC techniques to identify materials and process conditions that evaluate the suitability of photoresist strip exposure with respect to different metal gate electrode and high-k dielectric.

Using the simple diagram in FIG. 15, there are four possible trajectories through the process sequence. These four trajectories encompass all of the possible combinations of conventional and combinatorial processing illustrated. Those skilled in the art will understand that HPC techniques may be applied to other processes not illustrated such as anneal treatments, cleaning, rinsing, etching, surface treatments, surface functionalization, etc. As more variable process steps are included, the total number of required experiments increases dramatically. This illustrates the benefits of using HPC techniques to limit the number of substrates to a manageable number and minimize the cost of the development program.

Although the foregoing examples have been described in some detail for purposes of clarity of understanding, the invention is not limited to the details provided. There are many alternative ways of implementing the invention. The disclosed examples are illustrative and not restrictive.

What is claimed is:

1. A method for screening effective work functions, the method comprising providing a semiconductor substrate;
    forming a first oxide layer on the semiconductor substrate;
    defining a plurality of site isolated regions on the first oxide layer;
    patterning the first oxide layer in each site isolated region to form active areas on the semiconductor substrate by a first patterning process;
    forming a second oxide layer on the active areas;
    etching the second oxide layer in each site isolated region, wherein a thickness of the first oxide layer is varied in a combinatorial manner;
    forming a high-k dielectric layer on the second oxide layer on the semiconductor substrate;
    forming a metal layer on the high-k dielectric layer in each site isolated region, wherein at least one characteristic of the metal layer is varied in a combinatorial manner;
    patterning the metal layer to form metal electrodes by a second patterning process, wherein the metal electrode, the high-k dielectric layer, and the semiconductor substrate form a capacitor device in an active area;
    measuring an effective work function of the capacitor device formed within each site isolated region.

2. The method of claim 1 further comprising comparing the effective work function of the capacitor device in one site isolated region with the effective work function of the capacitor device in another site isolated region.

3. The method of claim 1 wherein the at least one characteristic of the metal layer comprises a material of the metal layer, a method of deposition, or a deposition condition.

4. The method of claim 1 wherein the second oxide layer is formed by thermal oxidation.

5. The method of claim 1 wherein a thickness of the second oxide layer varies between 1 nm and 6 nm between the plurality of site isolated regions.

6. The method of claim 1 wherein the high-k dielectric layer comprises one of hafnium oxide, hafnium silicon oxide, hafnium aluminum oxide, zirconium oxide, or a combination thereof.

7. The method of claim 1 wherein a thickness of the high-k dielectric layer is less than or equal to 2 nm.

8. The method of claim 1 wherein the electrode comprises one of TiN, TiAlN, or TiLaN.

9. The method of claim 1 further comprising annealing the semiconductor substrate after the forming of the metal layer.

10. The method of claim 1 further comprising annealing the semiconductor substrate after the forming of the metal electrodes.

11. A method for screening effective work functions, the method comprising
    providing a semiconductor substrate;
    forming a first oxide layer on the semiconductor substrate;
    defining a plurality of site isolated regions on the first oxide layer;
    patterning the first oxide layer in each site isolated region to form active areas on the semiconductor substrate by a first patterning process;
    forming a second oxide layer on the active areas;
    etching the second oxide layer in each site isolated region, wherein a thickness of the first oxide layer is varied in a combinatorial manner;
    forming a high-k dielectric layer on the second oxide layer on the semiconductor substrate, wherein at least one characteristic of the dielectric layer is varied in a combinatorial manner;
    forming a metal layer on the high-k dielectric layer in each site isolated region, wherein at least one characteristic of the metal layer is varied in a combinatorial manner;
    patterning the metal layer to form metal electrodes by a second patterning process, wherein the metal electrode, the high-k dielectric layer, and the semiconductor substrate form a capacitor device in an active area;
    measuring an effective work function of the capacitor device formed within each site isolated region.

12. The method of claim 11 further comprising comparing the effective work function of the capacitor device in one site isolated region with the effective work function of the capacitor device in another site isolated region.

13. The method of claim 11 wherein the at least one characteristic of the metal layer comprises a material of the metal layer, a method of deposition, or a deposition condition.

14. The method of claim 11 wherein the second oxide layer is formed by thermal oxidation.

15. The method of claim 11 wherein a thickness of the second oxide layer varies between 1 nm and 6 nm between the plurality of site isolated regions.

16. The method of claim 11 wherein the high-k dielectric layer comprises one of hafnium oxide, hafnium silicon oxide, hafnium aluminum oxide, zirconium oxide, or a combination thereof.

17. The method of claim 11 wherein a thickness of the high-k dielectric layer is less than or equal to 2 nm.

18. The method of claim 11 wherein the electrode comprises one of TiN, TiAlN, or TiLaN.

19. The method of claim 11 further comprising annealing the semiconductor substrate after the forming of the metal layer.

20. The method of claim 11 further comprising annealing the semiconductor substrate after the forming of the metal electrodes.

* * * * *